(12) United States Patent
Armstrong

(10) Patent No.: US 9,521,996 B2
(45) Date of Patent: Dec. 20, 2016

(54) SURGICAL RETRACTOR DEVICE

(75) Inventor: David N. Armstrong, Atlanta, GA (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/548,541

(22) Filed: Jul. 13, 2012

(65) Prior Publication Data

US 2013/0018228 A1    Jan. 17, 2013

Related U.S. Application Data

(60) Provisional application No. 61/507,166, filed on Jul. 13, 2011.

(51) Int. Cl.
- *A61B 1/32* (2006.01)
- *A61B 17/02* (2006.01)
- *A61B 17/00* (2006.01)

(52) U.S. Cl.
CPC .. *A61B 17/0218* (2013.01); *A61B 2017/00862* (2013.01); *A61B 2017/00867* (2013.01); *A61B 2017/0212* (2013.01); *A61B 2017/0225* (2013.01)

(58) Field of Classification Search
CPC .......................... A61B 17/3423; A61B 17/3431
USPC .................................................. 600/184–246
See application file for complete search history.

(56) References Cited

U.S. PATENT DOCUMENTS

| | | |
|---|---|---|
| 2,591,783 A | 4/1952 | Craddock |
| 3,863,639 A | 2/1975 | Kleaveland |
| 4,190,042 A | 2/1980 | Sinnreich |
| 4,889,107 A | 12/1989 | Kaufman |
| 5,080,088 A | 1/1992 | LeVahn |
| 5,460,170 A | 10/1995 | Hammerslag et al. |
| 5,522,790 A | 6/1996 | Moll et al. |
| 5,651,762 A | 7/1997 | Bridges |
| 5,704,372 A | 1/1998 | Moll et al. |

(Continued)

FOREIGN PATENT DOCUMENTS

| | | |
|---|---|---|
| EP | 0 586 580 B1 | 2/1998 |
| EP | 1987791 A2 | 11/2008 |

(Continued)

OTHER PUBLICATIONS

Kanamori et al., "Long-term survival of a baby with body stalk anomaly: report of a case", Surg. Today, 36 (1):98-102 (Jan. 2006).

(Continued)

*Primary Examiner* — Ellen C Hammond
*Assistant Examiner* — Christina Negrellirodrigue
(74) *Attorney, Agent, or Firm* — Woodard, Emhardt, Moriarty, McNett & Henry LLP

(57) ABSTRACT

Systems, devices, and methods capable of retracting organs are disclosed. In one embodiment, a retractor body comprises a deformable resilient frame defining a central opening and a deformable membrane extending across a portion of the central opening wherein the deformable resilient frame is arranged for complete disposal within the body of a patient and for varying the size of the central opening. In some exemplary embodiments, the retractor is arranged to form a helically coiled arrangement for insertion into the body of a patient. Delivery devices for delivering a deformable resilient retractor and methods of delivery are also disclosed.

16 Claims, 15 Drawing Sheets

(56) References Cited

U.S. PATENT DOCUMENTS

| | | | |
|---|---|---|---|
| 5,795,290 A | 8/1998 | Bridges | |
| 5,803,902 A | 9/1998 | Sienkiewicz | |
| 5,879,290 A | 3/1999 | Bridges et al. | |
| 6,042,539 A | 3/2000 | Harper et al. | |
| 6,063,025 A | 5/2000 | Bridges et al. | |
| 6,248,062 B1 | 6/2001 | Adler et al. | |
| 7,052,454 B2 * | 5/2006 | Taylor | A61B 17/3423 600/114 |
| 7,195,590 B2 | 3/2007 | Butler et al. | |
| 7,294,103 B2 | 11/2007 | Bertolero et al. | |
| 7,749,161 B2 | 7/2010 | Beckman et al. | |
| 7,766,824 B2 | 8/2010 | Jensen et al. | |
| 7,819,800 B2 * | 10/2010 | Beckman | A61B 17/3423 600/201 |
| 7,867,164 B2 | 1/2011 | Butler et al. | |
| 2006/0052669 A1 | 3/2006 | Hart | |
| 2006/0149306 A1 * | 7/2006 | Hart | A61B 17/3423 606/191 |
| 2007/0078477 A1 | 4/2007 | Heneveld, Sr. | |
| 2007/0088204 A1 * | 4/2007 | Albrecht et al. | 600/208 |
| 2007/0270654 A1 | 11/2007 | Pignato et al. | |
| 2008/0011307 A1 | 1/2008 | Beckman et al. | |
| 2008/0021362 A1 | 1/2008 | Fihe et al. | |
| 2008/0146883 A1 | 6/2008 | Kistler et al. | |
| 2008/0281161 A1 | 11/2008 | Albrecht et al. | |
| 2008/0281162 A1 | 11/2008 | Albrecht et al. | |
| 2009/0093752 A1 | 4/2009 | Richard et al. | |
| 2009/0137984 A1 | 5/2009 | Minnelli | |
| 2009/0227844 A1 * | 9/2009 | Hart | 600/208 |
| 2010/0094327 A1 | 4/2010 | Milsom | |
| 2010/0113883 A1 | 5/2010 | Widenhouse et al. | |
| 2010/0211093 A1 | 8/2010 | Abbate | |
| 2010/0280326 A1 | 11/2010 | Hess et al. | |
| 2011/0021879 A1 | 1/2011 | Hart et al. | |
| 2011/0054260 A1 | 3/2011 | Albrecht | |
| 2011/0092778 A1 * | 4/2011 | Butler et al. | 600/208 |
| 2011/0105848 A1 | 5/2011 | Sadovsky et al. | |
| 2011/0172495 A1 | 7/2011 | Armstrong | |
| 2012/0130184 A1 * | 5/2012 | Richard | 600/208 |
| 2013/0018229 A1 | 1/2013 | Jaworek | |

FOREIGN PATENT DOCUMENTS

| | | |
|---|---|---|
| EP | 2272436 A1 | 1/2011 |
| EP | 2275040 A1 | 1/2011 |
| GB | 1151993 A | 5/1969 |
| WO | WO 01/45568 A1 | 6/2001 |
| WO | WO 2004/030547 A1 | 4/2004 |
| WO | WO 2009/155537 A1 | 12/2009 |
| WO | WO 2012/087112 A1 | 6/2012 |

OTHER PUBLICATIONS

Kusafuka et al., "Gastroschisis reduction using "Applied Alexis", a wound protector and retractor", Pediatr. Surg. Int. 21(11):925-927 (Nov. 2005) Abstract.

Montero et al., "Single incision laparoscopic surgery (SILS) is associated with poorer performance and increased surgeon workload compared with standard laparoscopy", Am. Surg., 77(1);73-77 (Jan. 2011) Abstract.

Nozaki et al., "Glove-assisted laparoscopic radical nephrectomy: a novel technique", J. Laparoendosc. Adv. Surg. Tec A. 20(10):843-846 (Dec. 2010) Abstract.

Pearl et al., "Inexpensive self-retaining retractor for minor surgical procedures", Ann. Plast. Surg., 51(6):633-635 (Dec. 2003).

Tsang et al., "Denis Browne ring retractor in hypospadias surgery", Br. J. Urol., 76(4):510 (Oct. 1995).

* cited by examiner

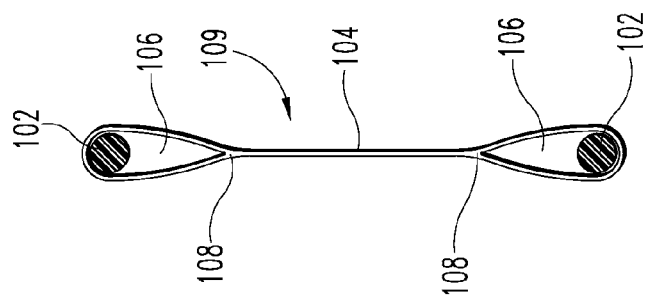
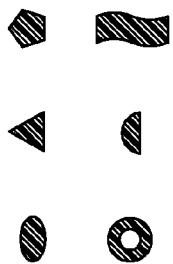
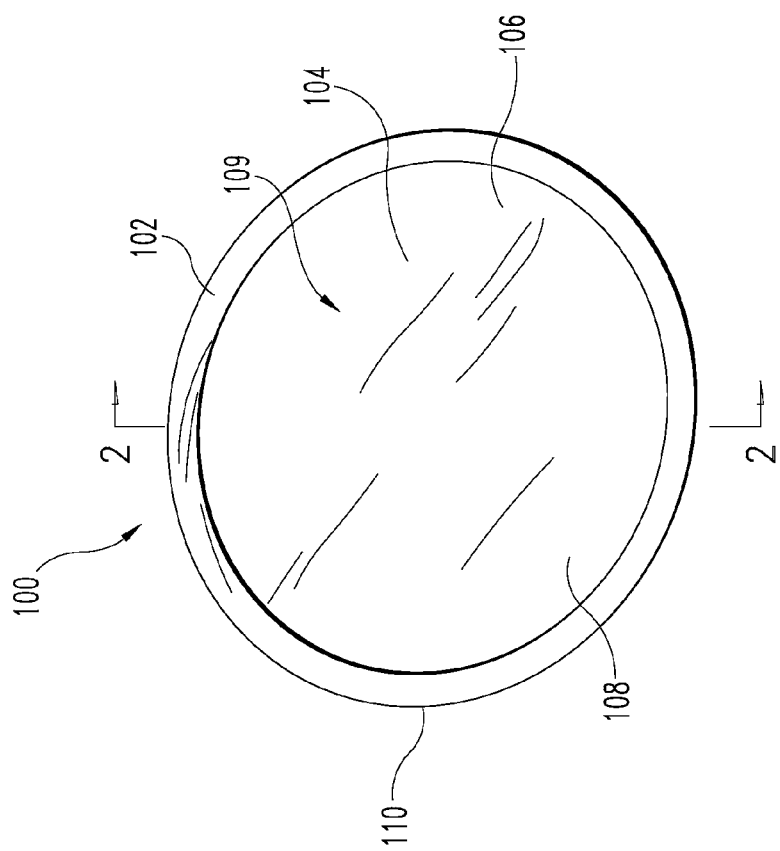

SURGICAL RETRACTOR DEVICE

CROSS-REFERENCE TO RELATED APPLICATION

This application claims the benefit of U.S. Provisional Application No. 61/507,166, filed on Jul. 13, 2011, which is hereby incorporated by reference.

FIELD OF THE INVENTION

The present disclosure pertains generally to retractors for retaining organs to provide working space during surgery, especially laparoscopic procedures.

BACKGROUND

One of the greatest technical challenges during hand-assisted laparoscopic surgery such as sigmoid colectomy or ileo-colic resection is retracting loops of small bowel which drop repeatedly into the surgical field and obscure visualization. The usual method to prevent this is positioning the operating table into steep Trendelenberg position, but this risks patient injury and positional hypotension. Devices to prevent prolapse of small bowel loops into the operative field during laparoscopic or open abdomino-pelvic surgery have been developed. For example, small bowel is known to be packed proximally in the abdomen using laparotomy pads or towels. Laparotomy pads or towels inadvertently left inside the abdomen, however, pose the risk of surgical complication with serious consequences. Other methods of retracting the small bowel into the upper abdomen utilize a plastic bag, into which the small bowel is placed and usually secured by means of a pull-cord around the opening of the bag. This approach does not provide retraction of the small bowel out of the pelvis and additionally risks strangulation of the bowel itself from constriction of the mesenteric blood supply.

Thus, new retracting devices and methods are desired.

SUMMARY

In one aspect, the invention pertains to a biocompatible deformable retractor comprising a deformable resilient frame and a deformable membrane. The frame comprises a border around a majority or all of a perimeter around a central opening with the membrane secured around at least a portion of the border to form a restraining structure across the central opening. The retractor is approximately planar or a non-planar convex shape in its natural un-deformed configuration. The retractor can have a round, square, oval, rectangular, oblong, or polyhedral shape. Alternatively, the retractor can have a composite shape such as bean, figure of eight, or U-shape. The various shaped retractors in a natural un-deformed configuration can have a perimeter of approximately 5 inches to 200 inches (12.7 cm to 508 cm). The frame has a cross-section through the frame, which can be can be round, oval, semi-circular, triangular, or polygonal having a perimeter from about 0.01 inch (0.25 cm) to about 3.94 inches (10 cm). The frame can be made, for example, from polymer, metal, or a combination thereof. In some embodiments, it may be desirable to have a cushion around the frame. The membrane can be made from a biocompatible sheet, fabric, net, or a combination thereof. In some embodiments, the membrane is transparent. In some embodiments, the retractor may have perforation through the membrane. The retractor in general can be self-extending.

In another aspect, the invention pertains to a method of using a retractor to retract one or more organs in a body cavity to form a working space in a living subject during a surgical procedure. The retractor can be deployed inside the body cavity by deforming the retractor, inserting the deformed retractor into the body cavity through a surgical opening, and releasing the retractor in the body cavity to retract the organ in the cavity to form the working space. Once deployed, the retractor can be self-retaining inside the cavity with the frame pushing against the wall of the cavity while the membrane presses against the organ to form the working space inside the cavity. In some embodiments, the deployed retractor has a convex shape pushing against the organ to make the working space. When a bean shaped retractor is deployed, the concave potion 120 of the bean shape can be placed over retroperitoneal vessel and/or conduit to prevent compression or occlusion of the vessel and/or conduit.

The surgical procedure can then be performed with assistance provided by the working space. In some embodiments, at least a portion of the membrane of the retractor remains attached to the frame throughout the procedure. During the procedure, the retractor may be repositioned to create different working spaces. Additionally, the membrane of the retractor may be punctured by laparoscopic instruments or laparoscopes if desired. After the surgical procedure, the retractor can be removed from the body cavity through the surgical opening. In one embodiment, the organ is GI tract, the body cavity is peritoneal cavity, and the working space is pelvic cavity. The surgical procedure may be a laparoscopic surgery or an open surgery. It may be a surgery of the GI tract, urinary system, reproductive system, abdominal wall, or pelvic floor. In some embodiments, the surgical procedure is open laparotomy, mini-laparotomy, pure laparoscopic surgery, hand assisted laparoscopic surgery, or single incision laparoscopic surgery.

In a further aspect, the invention pertains to a method of making a biocompatible deformable retractor. The method comprises securing a membrane to a biocompatible deformable resilient frame to form the retractor. In some embodiments, the frame is approximately planar or a non-planar convex shape in its natural un-deformed configuration. The frame generally forms a border around a majority or all of the perimeter of a central opening, and the membrane is secured around at least a portion of the border to form a restraining structure within the central opening. The retractor may be further attached to a wound retractor or a laparoscopic access device.

In some embodiments, a biocompatible retractor comprises a retractor body comprising a deformable resilient frame defining a central opening and a deformable membrane coupled to the deformable resilient frame and extending across a portion of the central opening; wherein the deformable resilient frame is arranged to vary the size of the central opening and is arranged for complete disposal within the body of a patient. In some instances, the biocompatible retractor further comprises a first portion of the resilient frame slidably coupled to a second portion of the resilient frame. Additionally, the biocompatible retractor may further comprise a first lumen defined by the first portion of the deformable resilient frame and arranged to receive the second portion. In some embodiments, the biocompatible retractor comprises a biasing member coupling portions of the retractor and may be arranged to bias the retractor into an expanded configuration. Additionally, or alternatively, the biocompatible retractor may comprise an insert.

In some aspects, the present disclosure teaches a biocompatible retractor for insertion beneath the skin of a patient comprising a retractor body comprising a deformable resilient frame defining a central opening and a deformable membrane coupled to the deformable resilient frame and extending across a portion of the central opening; wherein the deformable resilient frame is configurable between a contracted configuration and an expanded configuration arranged to retract tissue; wherein the contracted configuration is arranged for laparoscopic insertion through the skin of a patient; and wherein the is deformable resilient frame in the expanded configuration is arranged for complete disposal within the body of a patient. In some instances, the deformable resilient frame in the contracted configuration comprises an elongated arrangement. Similarly, in some instances, the deformable resilient frame may be helically coiled in the contracted configuration. Some embodiments of the present disclosure include a self-expandable deformable resilient frame that self-expands from the contracted configuration to the expanded configuration.

In some embodiments, a subcutaneous retractor delivery device for delivering a retractor beneath the skin of a patient comprises an elongated body comprising a proximal end region, a distal end region, and a retractor coupling portion positioned in the distal end region; wherein the retractor coupling portion is arranged to couple to a portion of a deformably resilient retractor; and wherein the retractor coupling portion is arranged to move the portion of the deformably resilient retractor between a first position outside of the body of the patient and a second position beneath the skin of the patient. The retractor may further comprise a first recess defined by the retractor coupling portion and arranged to receive the portion of the deformably resilient retractor. In some instances, the first recess opens away from the proximal end region of the elongated body and is arranged to push the portion of the deformably resilient retractor into the second position. Additionally, in some instances, a second recess defined by the retractor coupling portion and opening away from the distal end region of the elongated body and arranged to pull a portion of the deformably resilient retractor from the second position towards the first position. The retractor coupling portion may also be arranged for twistably coupling a portion of the resilient retractor to enable a twisting of the retractor with respect to the delivery device.

Further forms, objects, features, aspects, benefits, advantages, and embodiments of the present invention will become apparent from a detailed description and drawings provided herewith.

BRIEF DESCRIPTION OF THE DRAWINGS

FIG. 1 is a top plan view of a circular retractor with a deformable resilient frame and a transparent membrane secured around the frame.

FIG. 2 is a schematic diagram of a vertical cross sectional view along the b-b line of the retractor of FIG. 1 *a* showing round cross section of the frame with wrap around membrane, in which the vertical reference is relative to a horizontally oriented retractor frame.

FIG. 3 shows schematic diagrams of alternative cross section shapes of the frame.

DESCRIPTION OF THE SELECTED EMBODIMENTS

Figure 4B:
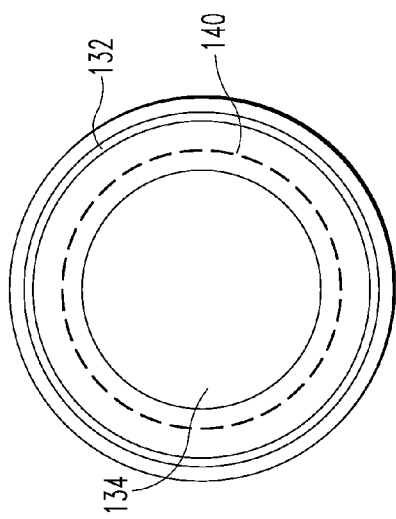
FIG. 4b is a schematic diagram of the circular retractor of FIG. 1 showing membrane secured around the frame with stitches.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

In some embodiments, the present disclosure teaches an expandable or contractible retractor, i.e., having an adjustable size. Furthermore, the retractor may be self-expanding or self-contracting. In some instances, the surgical retractor is expandable to provide added versatility to provide features suitable of a variety of applications. For example, in some embodiments, the expandable retractor may be shaped into different sizes and shapes to be suitable to surgical cavities of difference shape and sizes. The expandable retractor can also provide versatility during the delivery as well as the deployment and retrieval processes. Functions and embodiments of the expandable surgical retractors are described further in detail below.

In some instances, the retractors can be used in conjunction with a push-and-hook device. The push-and-hook type of device can be used to elongate the profile of the retractors so the retractor can be inserted, for example, through a trochar. Once inserted into the patient, the retractor is released to retract one or more organs. After the completion of the surgical procedure, the hooking element of the push-and-hook device can be used to retrieve the retractor from the surgical cavity through the trochar. In some embodiments, it may be particularly desirable to use the push-and-hook device to twist the retractor to provide a smaller cross section before the twisted retractor can be delivered.

The deformable resilient retractors and accessories, such as the push-and-hook device, described herein can provide easier access to surgical area during surgical operation by retracting non-relevant organs away from the surgical area. The retractors and accessories, in general can be used in a variety of surgical procedures including, for example, surgery of the GI tract, urinary system, reproductive system, abdominal wall, or pelvic floor. The retractors and its accessories described herein are applicable to surgical procedures including laparoscopic or open sigmoid colectomy, ileocolic resection, hysterectomy, pelvic floor repair or resection fixation, or repair of the rectum or bladder. The retractor and its accessories can be used for laparoscopic surgery as well as open surgery and is particularly suited for open laparotomy, mini-laparotomy, pure laparoscopic surgery, hand assisted laparoscopic surgery (HALS), or single incision laparoscopic surgery (SILS). Comparison of different laparoscopic surgeries are discussed in by Montero et al. in Am. Surg. 2011, 77(1):73-77, entitled: "Single Incision Laparoscopic Surgery (SILS) Is Associated with Poorer Performance and Increased Surgeon Workload Compared with Standard Laparoscopy," incorporated herein by reference. The retractor and its accessories can be used in human subjects or can be adapted for veterinarian use. The retractor and its accessories in general are biocompatible. The term "biocompatible" used herein refers to devices that are compatible with living cells, tissues, organs, or systems in the context of the uses described herein, and is effectively not cytotoxic or immunogenic. The biocompatible retractor and its accessories in general is sterile prior to use and can be distributed within sterile packaging.

One exemplary surgical procedure involves abdominal surgery. During abdominal surgery, small bowel loops can fall into the pelvis and lower abdomen if unrestrained, obscuring the surgical field. This is especially true during less invasive surgery such as HALS, SILS and other Laparoscopic procedures. The deformable resilient retractors described herein can be deployed inside the abdominal cavity and retract the small bowel out of the lower abdomen and pelvis, thus facilitating the surgery. In one embodiment, the retractor is inserted into a small laparoscopic incision by twisting the frame into a "figure-of-eight" shape and further folding the figure-of-eight upon itself to make a two layer circular configuration having about half the diameter of the original retractor. The retractor with reduced size can then be inserted into the peritoneal cavity where it "unfurls" and assumes substantially its original size and retracts small bowel out of the pelvic cavity.

The retractors described herein are applicable to other surgical procedures including laparoscopic or open sigmoid colectomy, ileocolic resection, hysterectomy, pelvic floor repair or resection fixation, or repair of the rectum or bladder. The improved deformable retractor in general can be inserted into the abdominal cavity of a patient undergoing surgery via a SILS, HALS or laparoscopic access device or even through an abdominal wall incision. Once deployed, a circular retractor assumes a generally ovoid shape within the peritoneal cavity, and is further "bent" into a convex form by pressure from the patient's lateral abdominal wall. During surgery, the retractor is held in place by means of anterior-posterior pressure exerted on the retractor by the anterior abdominal wall and posterior retroperitoneal structures. It is also held in place by lateral pressure exerted on it by the lateral abdominal wall and hence self-retaining. Having become "wedged" into the abdominal cavity, the membrane of the retractor exerts axial pressure on the abdominal viscera and prevents bowel loops from entering the surgical field. The retractor therefore applies forces in all three dimensions, hence can be referred to as a three-dimensional retractor.

The extent of compression exerted on the retractor and the eventual shape it adopts is determined by the size of the abdominal cavity, and the degree to which the peritoneal cavity is distended e.g., during laparoscopic or open abdominal surgery. The device can therefore be used both in "open" or "laparoscopic" abdominal surgery. The retractor can be placed in the abdominal cavity with a convex membrane surface facing toward the head of the patient to retract viscera in the axial plane and keep them out of the surgical field. In an alternative embodiment, the device is generally ovoid-shaped at rest, and is further compressed into an ovoid shape by anterior-posterior pressure from the anterior abdominal wall and retroperitoneum. The natural un-deformed configuration of the retractor can be a ring or other appropriate shape of soft "springy" malleable polymer or plastic, which prevents excessive pressure on the abdomino-pelvic viscera, but effectively keeps the viscera out of the surgical field.

The frame of the retractor can be made of biocompatible metal, polymer or a combination thereof. The frame can adopt any reasonable shape and size to better fit into body cavities of various sizes. For example, the retractor generally may be round, square, oval, rectangular, oblong, or polyhedral with a perimeter of approximately 5 to 200 inches (12.7 to 508 cm). Additionally, the retractor may be a composite shape such as bean, figure of eight, or U-shape. The retractor in general may be planar or non-planar with a convex three dimensional shape in its natural un-deformed configuration.

In some instances, the resting or non-deformed shape of the surgical retractors described herein can be planar or non-planar with convex shape and generally a circular or ovoid "ring" with a membrane. Once deployed inside a surgical cavity of interest, a deformable resilient frame contacts the inner wall of the cavity within the patient and supports the membrane attached such that the membrane forms a barrier against relevant organs inside the cavity therefore retracts or retains the organs to create a working space inside the cavity. Surgical procedure can then be performed inside the working space with the retained organs out of the way.

The different shaped retractor offers advantage to meet a variety of surgical needs. The retractor may additionally be attached to other instruments such as laparoscopic access device or a wound retractor to provide integrated access to surgical area of interest. As described further below, the frame may be made expandable to provide additional versatility.

The cross section through the frame, i.e., through the frame effectively perpendicular to an axis along the frame forming the general shape of the frame, may adopt various shapes and sizes to suite any particular needs also. The frame has a thin shaped member that forms a border of a central opening For example, the cross section through the frame may be round, oval, semi-circular, triangular, or polygonal and has a perimeter of about 0.25 cm to about 10 cm. A cushion, such as with a polymeric gel or soft elastic polymer can be used to pad around the frame to prevent damage to the wall of the body cavity during self-retaining deployment. In the embodiments where the expandable frame is involved, the frame of the retractors may be made tubular with a lumen where additional inserts, etc. may be added to modulate the properties and sizes of the retractor.

The membrane of the retractor that is attached to the frame can be made of a biocompatible sheet, fabric, net or a combination thereof. In general, the membrane is secured around the majority or all of the frame and at least a portion of the membrane generally remains attached to the frame while the retractor is being used in its retractor function. The membrane may contain perforations to provide access to the retracted organ during the surgery. Alternatively, the membrane can be made of material that can be punctured through by surgical instruments such as a laparoscope. A range of materials can be used for the membrane as described herein, and the membrane can be relatively impermeable or the membrane can have pores, or other opening, such as an open weave, as long as the membrane functions to restrain selected organs. In embodiments where the expandable retractor is involved, the membrane of the expandable retractor is made correspondingly expandable.

Structural Elements of the Retractor and Formation Thereof

The biocompatible retractor can have a deformable resilient frame with a deformable membrane secured around the majority or all of the perimeter of the frame to form a generally planar surface. The frame can be constructed out of resilient metal, polymer, or a combination thereof. The membrane may be a plastic sheet or the like, which serves as the retractor surface in the axial plane to retract for example viscera out of the pelvis. It can be desirable for the membrane to be transparent.

An embodiment of a retractor with a circular frame and a transparent plastic sheeting is illustrated in FIG. 1. Specifically, retractor 100 can comprise a frame 102 and a membrane 104 wrapped around portions of the frame 102 in a wrapped area 106, to secure the membrane 104, as shown in FIGS. 1-2.

The frame 102 can be a deformable frame capable of deformation in one or more directions while maintaining the structural integrity 102 of the frame. In some instances, the frame 102 is a deformable resilient frame that is capable of being deformed in one or more directions with a propensity to recover to an undeformed and/or lesser deformed configuration. Additionally, or alternatively, the frame 102 may have a shape-memory. For example, portions of the frame 102 may comprise shape memory materials, such as a shape memory alloy such as NiTi to name one non-limiting example.

The membrane 104 can comprise a material formed into a sheet and/or film-like arrangement. Other variations are also contemplated. The membrane 104 can comprise a series of elongated members, such as fibers, extending between portions of the frame 102, across the central opening 109. In some instances, elongated members extending across portions of the central opening 109 extend from a portion of the frame 102 to another elongated member, forming a mesh-like arrangement. As illustrated in several embodiments herein, the membrane 104 has a thickness substantially less than that of the frame 102. However, other variations are contemplated. For example, the membrane 104 and the frame 102 may have substantially the same thickness, or the membrane 104 may have a substantially greater thickness than that of the frame 102.

The wrapped area 106 of the membrane 104 can have sealing lines 108 securing portions of the membrane 104 to itself and portions of the membrane 104 around the frame 102. For example, sealing lines 108 can correspond with locations of heat bonding and/or adhesive bonding of the membrane 104 that form the wrapped portion of the membrane 104 extending around the frame 102 and securing the membrane 104 to the frame 102.

In some instances, the frame 102 comprises an elongated body following a path that defines a central opening 109. For example, frame 102 can comprise a relatively thin-walled member that forms the central opening 109 across which the membrane 104 extends. The retractor 100 can optionally have a segment 110 of the frame 102 that is free of attachment to the membrane 104. This segment 110 may leave expansion room for the membrane 104 during, for example, the deformation process of the retractor 100. Additionally, segment 110 may allow for a portion of the frame 102 to telescopically slide within another portion of the frame 102, so as to allow the size and/or shape of the frame 102 and/or central opening 109 to change. However, it is contemplated that the membrane 104 can be attached completely around the frame 102 in some embodiments.

In general, the frame 102 can form a closed structure around the central opening 109 or an open structure, following less than the perimeter of the central opening 109. The frame 102 can form a planar arrangement in its relaxed position, or the relaxed position of the frame 102 can form a non-planar convex shape. In some instance, the perimeter formed by the frame 102 provides for attachment of the membrane 104 across the central opening 109 or a suitable portion thereof. As noted above, the membrane 104 may or may not be attached to itself and/or to the frame 102 at all portions of the perimeter of the central opening 109. In some embodiments, the membrane 104 is attached around substantially all of the perimeter.

Figure 6B:
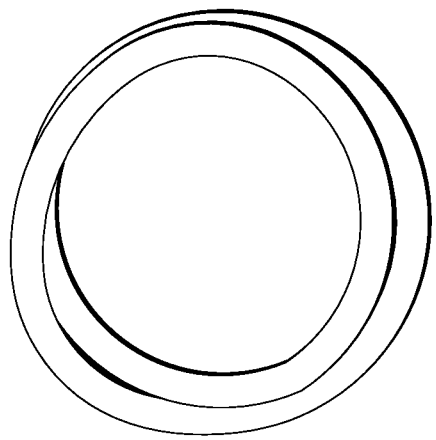
FIG. 6b is an illustration of the retractor of FIG. 6a, folded into a two layer deformed configuration.

A cross sectional view through the retractor 100 of FIG. 1 along the 2-2 line is illustrated in FIG. 2. As illustrated, the membrane 104 is wrapped around the frame 102 in the wrapped area 106 and is secured to itself by sealing lines 108. In some instances, the frame 102 has a circular or round cross-section, as illustrated in FIG. 2. The frame 102, however, may have a number of cross-sectional shapes at portions along the length of the frame 102 such as triangular, oval, pentagonal, wavy rectangular, semi-circular, or circular with hollow, as shown in FIG. 3. In general, as will be appreciated by one of ordinary skill in the art, any reasonable cross sectional shape of the frame 102 can be used. Frame 102 having a triangular and/or wavy rectangular cross section, in particular, may provide better self-retaining properties for the retractor 100 once the retractor 100 is deployed, as the triangular and/or wavy rectangular cross-section may provide greater latch when in contact with wall of the body cavity. Additionally, in the embodiments where the cross-sectional shape of the frame 102 is semi-circular or triangular, twisting and folding the semi-circular or triangular frame 102 into a two layer configuration, as illustrated in FIG. 6b, results in a circular or diamond cross sectional profile, which further assists in inserting the retractor 100 into the abdominal incision.

The cross section of the frame with a circular cross section can measure from about 0.1 cm to about 3 cm in diameter, in some embodiments from about 0.25 to about 2.5 cm, and in additional embodiments about 0.5 cm to about 2 cm in diameter. For frames with alternative cross sectional shapes, the size of the cross section is more easily defined with the perimeter instead of diameter. In general, the frame can have a perimeter around a cross section of the frame of about 0.25 cm to about 10 cm, in some embodiments of about 0.5 cm to about 8 cm, and in additional embodiments of about 1 cm to about 6 cm. A person of ordinary skill in the art will recognize that additional ranges of diameters and perimeters within the explicit ranges above are contemplated and are within the present disclosure.

Figure 4D:
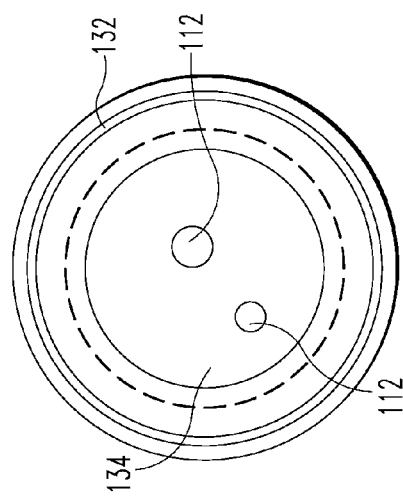
FIG. 4d is a schematic diagram of a round shape retractor having perforations on the membrane.
Figure 4A:
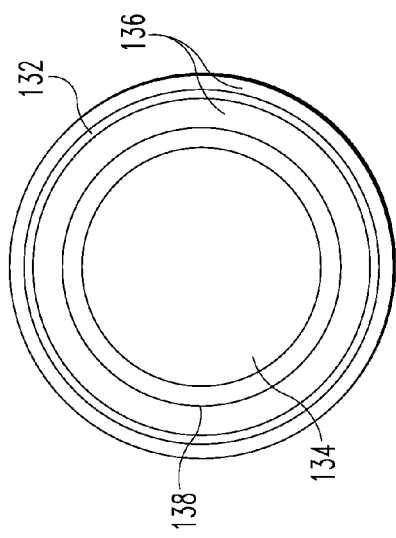
FIG. 4a is a schematic diagram of the circular retractor of FIG. 1 showing membrane secured around the frame with an adhesive.
Figure 4C:
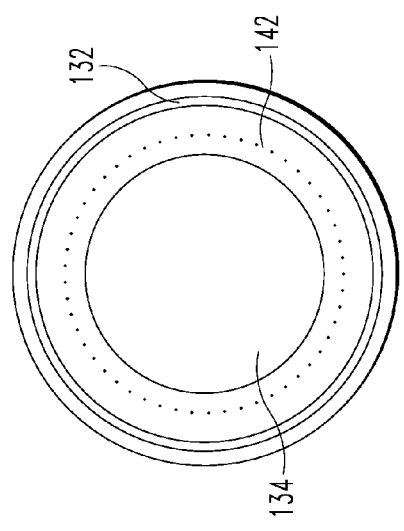
FIG. 4c is a schematic diagram of the circular retractor of FIG. 1 showing membrane secured around the frame with staples

In some embodiments, the membrane 104 is coupled to the frame 102 using a coupling member such as an adhesive and/or heat sealing techniques, although other techniques known in the art may also be used. Alternatively, or additionally, the membrane 104 may wrap around the frame 102 and attach or seal to itself as shown in FIGS. 1 and 2. The wrap around configuration with various sealing methods is further illustrated by schematic diagrams in FIGS. 4a-d. Referring to FIG. 4a, membrane 134 wraps around frame 132 creating a wrapped around area 136 around the frame 132 that is secured by sealing line 138, which is the point of attachment of the membrane 134 onto itself, such as via adhesive or heating of the membrane 134 material. Alternatively, the sealing line 138 may be created with stitches 140 as shown in FIG. 4b or with staples 142 as shown in FIG. 4c. While these figures show the membrane 134 attached to itself after wrapping around the frame 132, in additional or alternative embodiments, the membrane 134 can be directly attached to the material of the frame 132. Thus, the membrane 134 material can be glued, heat bonded, stitched and/or stapled directly to the frame 132. In general, the membrane 134 can be attached around a majority of the perimeter of the frame 132, although the membrane 134 may be attached around the entire perimeter of the frame 132.

The frame of the retractor in general can be composed of resilient, flexible material to permit twisting, bending, and generally deformation of the retractor. Padding or cushion can be added around the frame to improve traction between the retractor and the wall of the body cavity while preventing applying excess pressure to cause injury to the tissue of the cavity.

In general, the frame can be formed from one or more biocompatible materials, including, for example, metals, such as stainless steel or alloys, e.g., Nitinol®, or polymers such as polyether-amide block co-polymer (PEBAX®), nylon (polyamides), polyolefins, polyesters, polycarbonates or other suitable biocompatible polymers including elastomeric polymer, such as suitable polyurethanes, polydimethyl siloxane, acrylonitrile butadiene styrene (ABS), high density polyethylene (HDPE), rubber, polyisoprene (i.e., synthetic rubbers), and polytetrafluoroethylene. Spring metals or shape memory metals, such as Nitinol®, can be particularly useful. A metal frame can be covered in a polymeric cover or the like. In some embodiments, different portions of frame can be formed from different materials to introduce desired stiffness/flexibility for the particular portion of the frame. In some embodiments, the frame can be made from polymer embedded with metal wire. Suitable polymers include, for example, polyamides, i.e., nylons. The metal wire can be braided, coiled or otherwise placed over a polymer tubing liner with some tension. A polymer jacket can be then placed over the top of metal wire or the like. Upon heating over the softening temperature of the polymer and subsequent cooling, the wire becomes embedded within the polymer. The liner and jacket can be the same or different materials. The wire adds additional mechanical strength while maintaining appropriate amounts of flexibility. In general, the frame is made of material that has sufficient resilience to substantially regain its resting configuration after being deformed, which is self-extendable. The frame may be a durometer from about 40 A to about 90 A on the A durometer scale or from about 50 D to about 90 D on the D durometer scale, as specified in ASTM protocol D2240-00. Frames formed from elastic polymers, such as rubbers or the like, can be convenient and relatively inexpensive.

The membrane can be constructed from a biocompatible sheet, fabric, net, or a combination thereof. The membrane may be made out of transparent or semi-transparent materials, such as polymers. In some embodiments, it may be desirable to have perforation on the membrane for the purpose of passing surgical instruments such as laparoscope through the membrane. FIG. 4d, for example, shows a schematic diagram of a round shaped retractor with perforations 112 on the membrane. The membrane can alternatively be constructed from material that can be punctured by medical instruments such as a laparoscope to gain better visualization from trochar sites proximal to the retractor.

The membrane may be clear, transparent, translucent, opaque and made of a variety of different materials with different characteristics. In one embodiment, the membrane can be made from an elastomer such as polyisoprene, polyurethane, silicone polyurethane, or silicone. In some embodiments, the membrane may be non-elastic or slightly elastic so that the membrane can restrain organs or other body portions without significantly distending the membrane. Thus, inelastic materials such as polyethylene terephthalate can be used to form the membrane or portions thereof. The thickness of the membrane may vary, for example, from about 0.005 inches (0.0127 cm) to about 0.1 inches (0.254 cm) and in some embodiments of about 0.01 inches (0.0254 cm) to about 0.05 inches (0.127 cm). A person of ordinary skill in the art will recognize that additional ranges of thickness within the explicit ranges above are contemplated and are within the present disclosure.

The membrane in general is foldable and has sufficient strength to retain organ while being extended across the central opening and/or around the frame. The retractor can be made of disposable materials, such that the retractor may be thrown away after use, although the retractor can be made of a durable, reusable material in some embodiments.

The resilient nature of the frame permits twisting and folding of the retractor to allow insertion into small abdominal wall incisions, and permits the retractor to conform to the inner contours of the inner aspect of the patient's abdomen to effectively retract bowel away from the surgical field. Clinical experience has demonstrated that during open abdominal laparotomy in an approximately 70 kg male the abdominal cavity measures approximately 6-8 inches in anterior to posterior (A-P) plane and 10-12 inches in lateral plane. Thus, for a circular-shaped retractor for a majority of patients, the natural or "resting" dimensions of the retractor can have a suitable diameter of approximately 6 to 20 inches, in some embodiments from about 8 to about 18 in and in additional embodiments from about 10 to about 16 inches in diameter. For a generally convex-shaped retractor used for open surgeries, the resting A-P dimensions within the patient can be from about 2 to about 12 inches, in some embodiments from about 4 to about 10 inches and in further embodiments from about 6 to about 8 inches. Lateral dimensions, across the patient, of a generally non-planar convex shaped retractor within the patient can be about 6 to about 20 inches, in further embodiments from about 8 to about 18 inches and in other embodiments form about 10 to about 16 inches. A person of ordinary skill in the art will recognize that additional dimensional ranges within the explicit ranges above are contemplated and are within the present disclosure.

Furthermore, clinical experience has demonstrated that during laparoscopic surgery in an approximately 70 kg male, A-P peritoneal dimensions are 9-12 inches and lateral dimensions are 10-12 inches. The lateral dimensions are similar to open cases, since laparoscopic insufflations of the abdomen increases the A-P dimension much more than the lateral dimensions, which stays reasonably unchanged. For a circular retractor, the natural or "resting" dimensions of the retractor has a diameter from about 6 to about 24 inches, in further embodiments from about 8 to about 20 and in other embodiments from about 10 to about 16 inches. For a generally convex-shaped retractor within the patient used for laparoscopic cases, the resting A-P dimensions can be in some embodiment from about 6 to about 20 inches, in further embodiments from about 8 to about 18 inches and in other embodiment from about 9 to about 14 inches. Lateral dimensions for a generally ovoid retractor within the patient would be approximately the same as for an "open" version of the retractor i.e., from about 6 to about 20 inches, in further embodiments from about 8 to about 18 inches and in additional embodiments from about 10 to about 16 inches. A person of ordinary skill in the art will recognize that additional ranges of dimensions for non-circular embodiments within the explicit ranges above are contemplated and are within the present disclosure.

Figure 5G:
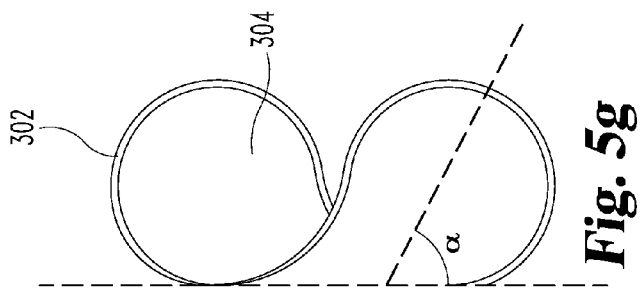
FIG. 5g is a schematic diagram of a retractor with a natural non-planar convex shape.
Figure 5D:
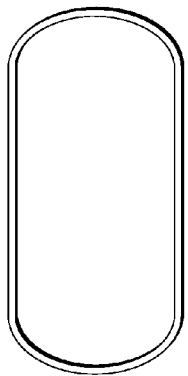
FIG. 5d is a schematic diagram of planar retractor of oblong shape.
Figure 5E:
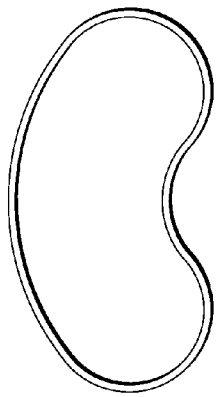
FIG. 5e is a schematic diagram of planar retractor of bean shape.
Figure 5F:
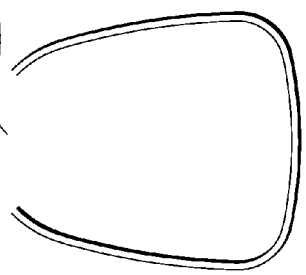
FIG. 5f is a schematic diagram of planar retractor of "U" or horse shoe shape.
Figure 5A:
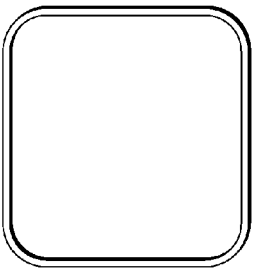
FIG. 5a is a schematic diagram of planar retractor of square shape.
Figure 5B:
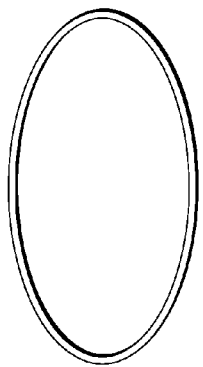
FIG. 5b is a schematic diagram of planar retractor of oval shape.
Figure 5C:
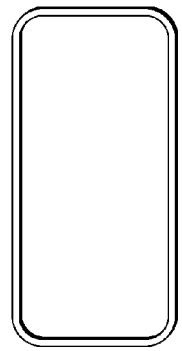
FIG. 5c is a schematic diagram of planar retractor of rectangular shape.

Besides round or circular shape, alternative planar retractor shapes such as square, rectangle, oval, oblong, bean, and "U" or horse shoe or composite shape shown in FIG. 5a-f, can be adopted. Some of these frame shapes form a closed structure around the interior. The frame of the "U" or horse shoe shaped retractor does not surround the perimeter of the membrane and has an opening area 122 that can be more easily deformed than other parts of the retractor. Additionally, the retractor can be made with a frame that is non-planar in its resting or natural configuration. An example of a non-planar convex circular retractor is shown in FIG. 5g, although retractors with other shapes can be made three dimensionally convex also. The degree of curvature out of the plane can be selected to suit desired properties of the retractor. The non-planar convex shaped retractor may be desirable in some applications, as the retractor may or may not rely on the interaction between the wall and the frame only to create the convex shape for restraining the organs within the patient. The dimensions of the frame of a non-planar retractor can be evaluated by distorting the frame to a planar configuration for the measurements, and then the measurements described above for the naturally planar retractors can be applied to the non-planar designs.

In general, the retractor can be made of various sizes and configurations for use in various size humans and animals depending on the size and weight of the individual (e.g. small, medium and large), body habitus, prior abdominal surgery, size and dimensions of the peritoneal cavity, and whether open vs. laparoscopic surgery is being performed. For example, when deployed inside a body cavity, the concavity of a bean shaped retractor may be placed over retroperitoneal vessel and/or conduit to prevent compression or occlusion of the vessel and/or conduit. For devices of alternative shapes, the size of the retractor is more conveniently defined with the perimeter instead of diameter. In general, the retractor can have a perimeter from about 5 to about 200 inches (12.7 to 508 cm), in some embodiments from about 10 to about 150 inches (25.4 to 381 cm), in additional embodiments from about 20 to about 100 inches (50.8 to 254 cm). A person of ordinary skill in the art will recognize that additional ranges of perimeter within the explicit ranges above are contemplated and are within the present disclosure.

In some instances, portions of the retractor 100, such as the frame 102, are arranged for complete disposal within the body of a patient (e.g., beneath the skin of the patient). For example, in some embodiments, the frame 102 of the retractor 100 is arranged for complete disposal within the abdomen of a patient. Additionally, or alternatively, some embodiments of the present disclosure lack a portion that extends outside of the body of the patient. In some instances, the deformable resilient frame lacks a portion that extends outside of the body of the patient, such as a handle. However, it is contemplated that insertion and/or retrieval portions of the retractor 100 and/or an accessory, such as a push-and-hook type device discussed below, may extend to a position outside of the body of the patient (e.g., extending through the abdominal wall and the skin of the patient to a position outside of the patient's skin).

The retractor may additionally be combined with other surgical instruments such as a wound retractor or a laparoscopic access device. In one embodiment, the retractor may affix to the proximal aspect of an abdominal wound retractor such as the "Alexis" retractor by Applied Medical, hand-assisted laparoscopic access devices such as the "Gelport" also from Applied Medical, or the "Dextrus" hand access device from Ethicon Endosurgery. The wound retractor and the access devices commonly has an inner plastic or polymer ring that can partially retain the retractor in the abdominal wound. The retractor described herein may attach to a selected location of the ring of the wound access device using an approximately clip-on attachment which attaches the retractor to the inner ring of the abdominal wound retractor. Such a clip-on attachment can attach around the inner ring, while not interfering, impinging or perforating the sleeve aspect of the abdominal wound retractor and retracts viscera into the upper abdomen. Various fasteners can be adapted for interfacing the surgical retractor described herein with the wound access retractor lower ring. The interfacing of the surgical retractor with the wound retractor provides for ability to obtain the advantages of both devices while limiting any interference between the devices.

The retractor described herein can be made to be disposable items to avoid the need for subsequent cleaning and sterilization. The generally sterile biocompatible retractor may additionally be coated with bacterialcidal or anti-inflammatory agents to further prevent infection or other complication during the surgical procedure. In some embodiments, it may be advantageous to make the retractor impermeable to fluids to provide a relatively dry environment in the working space.

Expandable Retractor

Various embodiments of the disclosed retractors can be made expandable to provide additional versatility to suit the needs of a variety of applications. In some embodiments, the expandable retractor may be shaped into different sizes and shapes to be suitable to surgical cavities of difference shape and sizes. The expandable retractor can also provide versatility during the delivery as well as the deployment and retrieval processes.

Figure 9:
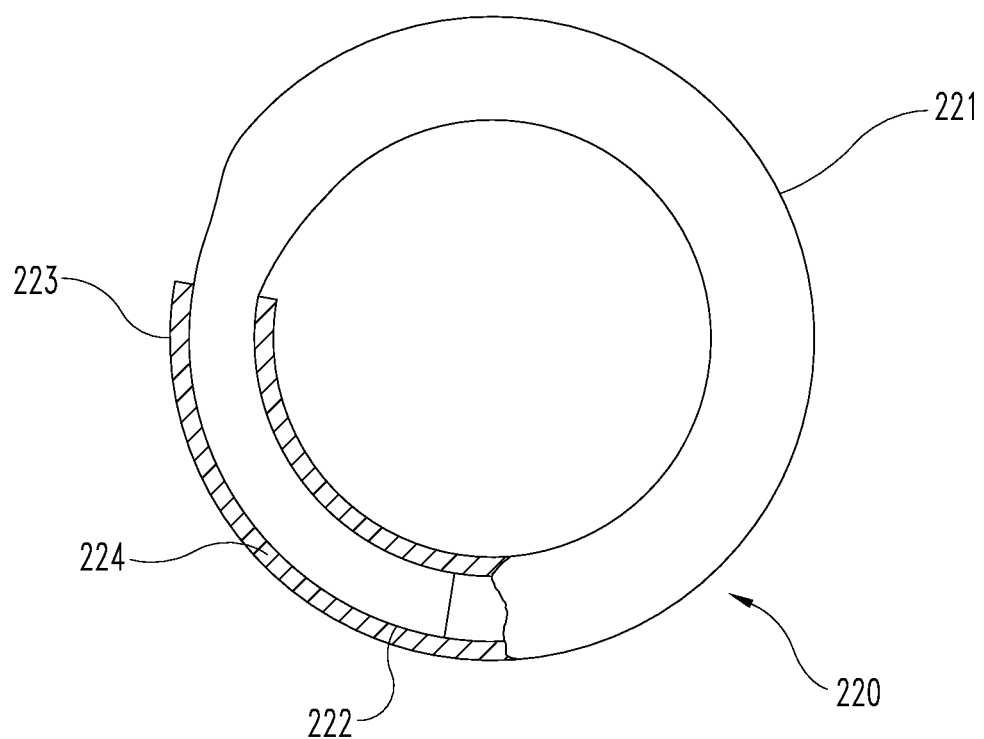
FIG. 9 is a partial cross-sectional top view of one embodiment of a deformable resilient frame.

In one embodiment, the retractor can be made expandable to a larger diameter, or to a different shape. The frame as well as the membrane can be made expandable to a greater surface area, or a different shape or shapes. Referring to FIG. 9, in one embodiment, an expandable retractor 220 comprises a tubular ring 221 with one end 222 of the tubular ring 221 having a slightly smaller diameter than the opposite end 223. The smaller diameter end 222 of the tubular ring 221 is inserted into the larger diameter end 223 to have a slidably overlapping section 224 to create a generally circular ring. The overlapping section 224 may be large or small. In some embodiments, the overlapping section 224 can comprise part or more than 50% circumferences of the tubular ring 221. When the smaller diameter end 222 is slid into the larger end 223 to increase the size of the overlapping section 224, the expandable retractor 220 contracts in size. Conversely, the smaller end 222 may be withdrawn out of the larger tubular member end 223 to reduce or diminish the overlapping section 224 to create an expandable retractor 220 with a larger diameter and surface area.

In some embodiments, the retractor ring comprises a series of segments of tubular members with incrementally decreasing diameters, wherein the transition from a larger to a smaller diameter is by means of a "step down" or "shoulder" from the larger to the smaller diameter segment. In some embodiments the "step downs" or "shoulders" are also present on the smaller diameter end of the retractor ring. In this embodiment, the retractor ring may be expanded serially from one "step down" or "shoulder" to the next, and the ring will be held in place by means of the shoulders abutting against each other to prevent the ends of the ring from slipping within each other and loss of retractor diameter to keep the retractor in a pre-determined expanded diameter. This embodiment may be manufactured by inserting a plurality of tubular members within each other, wherein the outer diameter of the smaller member is the same as the inner diameter of the larger tubular member. Having inserted the smaller diameter member within the larger diameter member the members are affixed. This is repeated a plurality of times resulting in a series of tubular members of decreasing inner and outer diameters, wherein the "step down" or "shoulders" on the inner and outer aspects are staggered along the length of the final tubular structure. The smaller diameter end of the resulting tubular device is then inserted into the larger diameter end, resulting in a ring device. As the ring is expanded, it is held in place by the outer and inner "shoulders" abutting against each other.

In a further embodiment, there are "ratchets" located at points along the circumference of the outer and inner tubular member. This "ratchet" configuration holds the inner and outer tubular member at a given diameter, and prevents the inner tube from unintentionally advancing further into the outer tubular member and thereby decreasing the diameter of the retractor. The "ratchet" mechanism therefore holds the retractor ring at any pre-determined diameter, so facilitating retraction of the peritoneal contents.

Figure 10:
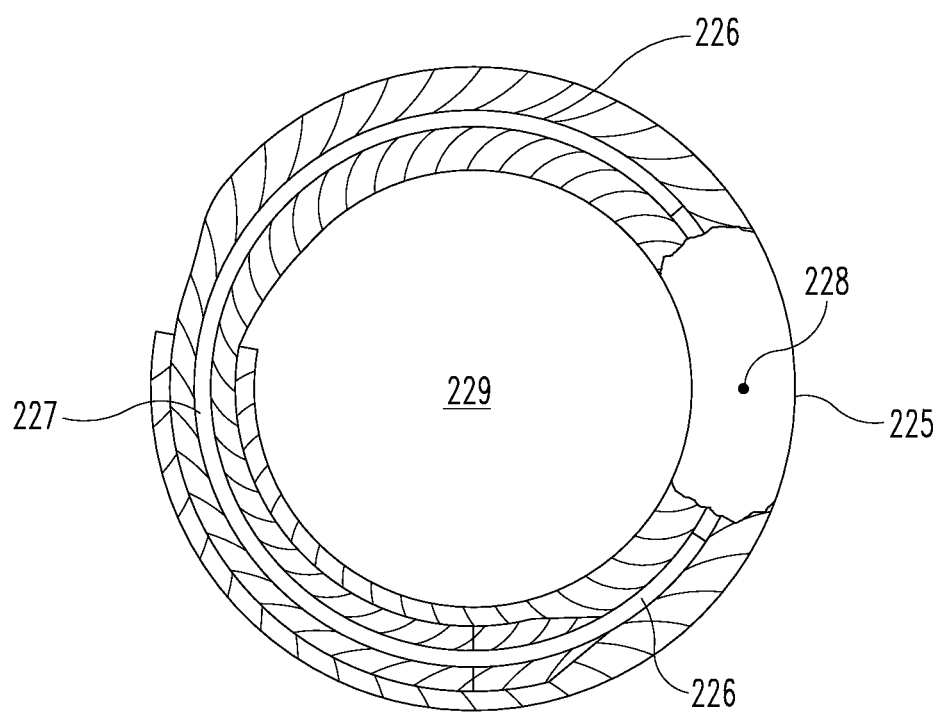
FIG. 10 is a partial cross-sectional top view of one embodiment of a deformable resilient frame having an insert.
Figure 11:
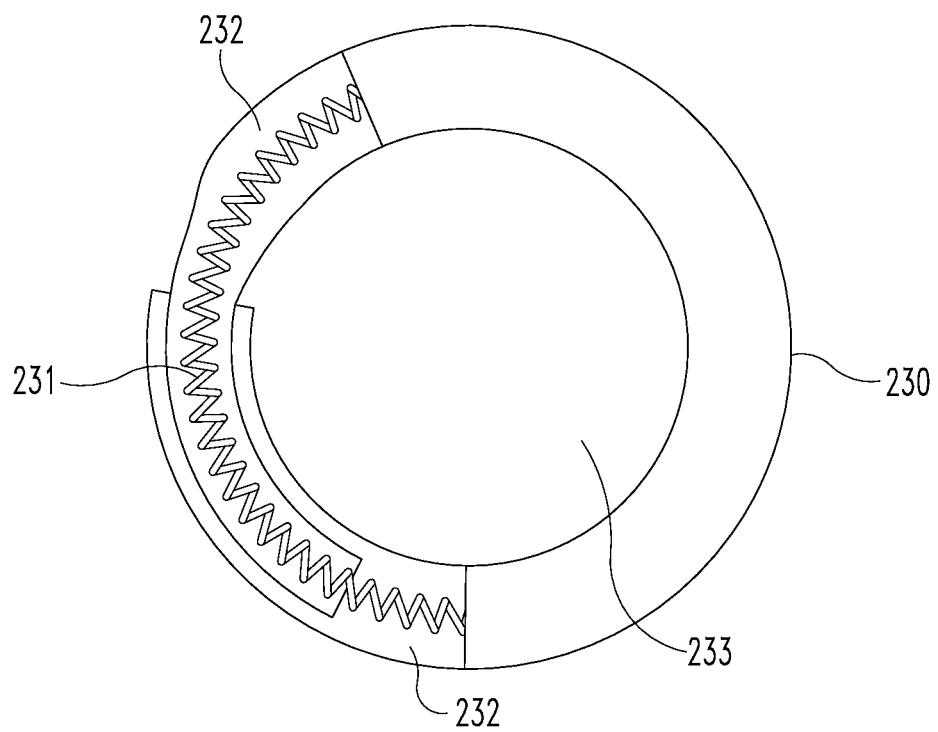
FIG. 11 is a partial cross-sectional top view of one embodiment of a deformable resilient frame having a biasing member.

In a further embodiment, referring to FIG. 10, all or part of the tubular member 225 may be hollow. An insert 226, such as a reinforcing member, can be used to add the required properties of malleability flexibility or shape memory properties to the tubular member 225. In this embodiment, the insert 226 may be present throughout part or all of the circumference of the outer tubular member 225 or throughout a portion of the hollow outer ring, depending on whether the hollow outer ring is fully contracted and/or closed (i.e. smallest diameter) or fully expanded (i.e. largest diameter).

To avoid disconnection, the midpoint 227 of the insert 226 and the midpoint 228 of the tubular member 225 are located preferably 30-330 degrees apart, more preferably 90-270 degrees apart or most preferably approximately 180 degrees apart, to prevent the disruption of the retractor. In a further embodiment, the insert 226 may also be partially or completely hollow to allow the ends of the insert 226 to slide in and out as the retractor is contracted, expanded, closed, and/or opened.

Both or either the insert 226 and the tubular member 225 may be made of metal, polymer, or a combination thereof to have the desired flexibility malleability bending twisting or shape memory properties to provide the desired performance of the ring retractor as a whole.

Additionally, the retractor may assume different shapes in its contracted and/or expanded configurations. In one embodiment, the retractor may be a circular shape in its contracted configuration, and expand into an oval configuration in the expanded configuration and/or as the retractor is expanded. Any combination or mixture of shapes may be provided as the retractor is expanded and contracted, in order to provide the desired size and shape retractor to provide the preferred retraction of the intra-abdominal organs in individual sized patients.

The central opening and the membrane expand and contract as the outer ring is made larger and smaller or as the ring assumes a variety of different shapes. In one embodiment, the membrane 229 is made of a rubber type material, similar to that found in elastic balloons, which freely expands and contracts. This expandability also provides the necessary flexibility of the membrane 229 to allow it to be folded and twisted into different shapes, for instance twisted into a figure-of-eight then folded upon itself to make a retractor approximately half of its original size.

In yet a further embodiment, the retractor ring 230 may be expandable by a device or method such as a spring 231 located within the lumen of the outer ring 232 as described above. In this embodiment, the ring 230 may expand by means of force exerted from a compressed spring 231 located within the outer ring 232 with corresponding increase in the surface area of the membrane 233 of the retractor. Conversely, contraction of the ring 230 (i.e., making the ring smaller) results in compression of the contained spring 231. In this embodiment, the contracted and/or closed retractor ring 230 is insertable into the abdomen, since this arrangement has a smaller maximum outer dimension than the expanded arrangement.

In general, the expandable retractors described herein can be delivered or deployed using the push-and-hook device and methods described below. Specifically, the expandable retractor may be twisted into a figure-of-eight and folded upon itself. After inserting the retractor into the abdomen the retractor "unfurls" to its planar form, and may then be further expanded by means of the contained mechanism, such as the spring 231 or insert 226, to further increase the surface area of the central opening and/or the membrane.

To prevent complete opening of the retractor rings, and potential loss of the contained spring 231, mechanical "stops" are configured within the circumference of the rings of the expandable retractors, which limits the minimum and maximum diameter the retractor may reach.

Having inserted the ring retractor into the body cavity, the retractor "unfurls" to its resting shape, and may then be further "opened" or expanded by a combination of laparoscopic graspers, manually (as in hand assisted surgery) or a combination of both. In a further embodiment, protrusions are present at locations around the retractor ring which can be grasped by laparoscopic instruments to facilitate opening or expanding the ring. Depending on the size of the surgical cavity of interest, the size the expandable retractor can be adjusted such as using the "shoulder" mechanism described above.

Alternative embodiments include other means of expanding the ring such as infusion of gas or liquid into the lumen of the ring, so expanding the diameter of the ring. Alternative embodiments include a method or device to automatically open the ring, such as a "release" mechanism incorporated into the outer ring and spring interface. Pressing the release mechanism then allow the spring to open and thereby widen or expand the retractor ring.

Push-and-Hook Device

Figure 12:
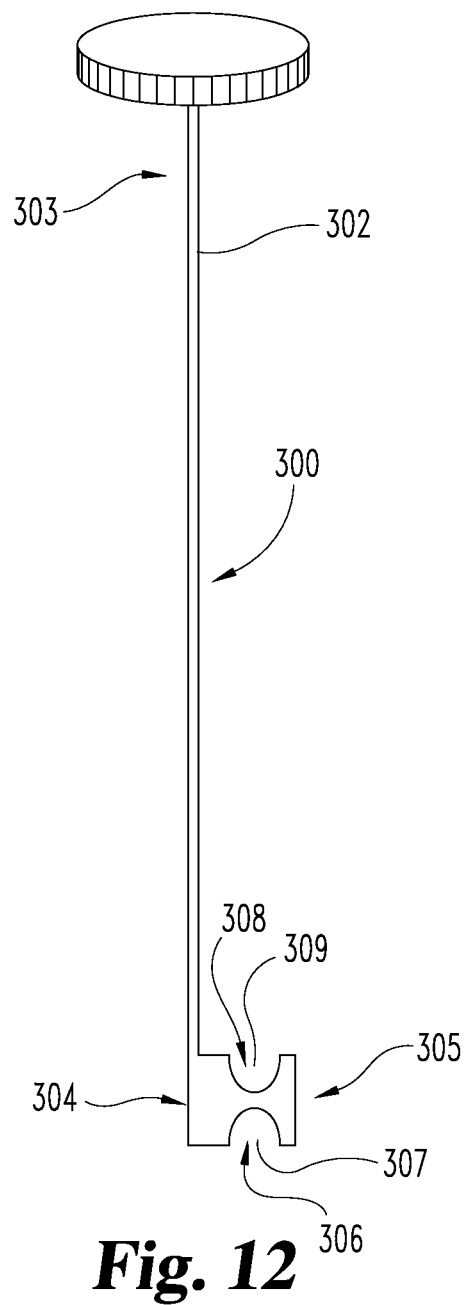
FIG. 12 is a front elevational view of one embodiment of a delivery device.
Figure 13:
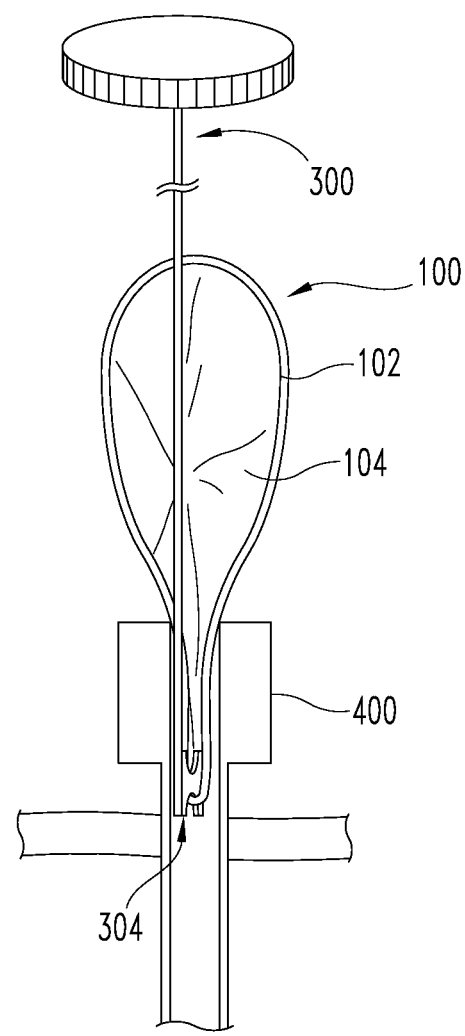
FIG. 13 is a front elevational view of a one embodiment of a deformable resilient retractor being advanced through an access device.

A push-and-hook type of device (hereinafter the PH device) can be used to facilitate the delivery and retrieval of the surgical retractors of interest during surgical procedures. In some instances, the PH device can be used to elongate the profile of a retractor so the retractor can be inserted through a trochar. Once inserted, the retractor is released to retract organ. After the completion of the surgical procedure, the retractor can be retrieved with the PH device through the trochar. In some embodiments, the PH device may be used to twist the retractor before the twisted retractor can be delivered. Referring to FIG. 12, in one embodiment, the PH device 300 has a shaft 302 comprising a proximal end region 303, a distal end region 304, and a retractor coupling portion 305. In some embodiments, the retractor coupling portion 305 comprises an inserting portion 306 arranged to insert a portion of the retractor 100. In some instances the inserting portion 306 comprises a recess arranged to receive a portion of the retractor 100. For example, the inserting portion 306 may comprise an "n" shaped pusher hook 307 that can be used to push a retractor through a trochar 400 during the insertion or delivery process. In some embodiments, the retractor coupling portion 305 comprises a retrieving portion 308 arranged to retrieve a portion of the retractor 100 from inside of the body of a patient, such as retrieving a portion of the retractor 100 into and/or out of the trochar 400. In some instances, the retrieving portion 308 is proximal to the insertion portion 306, such as the "n" shaped hook 307. Additionally, or alternatively, similar to the inserting portion 306, the retrieving portion 308 can comprise a recess arranged to receive a portion of the retractor 100. In some instances, the retrieving portion 308 comprises a "u" shaped retrieval hook that can be used to retrieve the retractor 100 and, in some cases, pull it out from the surgical cavity via the trochar 400. The diameter, shape and size of inserting portion 306 and/or retrieving portion 308 and/or hooks 307 and 309 can be the same or slightly larger than the diameter of the frame 102 of the retractor 100.

In one embodiment, to enable the retractor 100 to be inserted through a standard 12 mm operative trochar 400, the peripheral frame 102 of the retractor 100 can have a maximum diameter of 5 mm, and optionally a hemispherical cross-section such that two sections of the frame 102 can be brought together to roughly form a spherical cross section with a corresponding small overall cross section in the deformed configuration. As shown in FIGS. 13-16, the PH device 300 consisting of the shaft 302 (in some instances 1 mm diameter) is detachably affixed in the coupling portion 305 of the distal end region 304 to the frame 102 via the inserting portion 306, such as the coupling "n" shaped hook 307, and can simply push a portion of the retractor 100 through the operative trochar 400 into the peritoneal cavity. When the retractor 100 exits the distal end region of the trochar 400 it can open up to provide retraction of the abdominal contents, and the PH device 300 is simply removed from the trochar 400.

In some instances, a hemispherical cross section of the frame 102 of the retractor 100 can form a generally circular profile when portions of the frame 102 are brought into adjacent position, such as when the retractor is compressed within the operative trochar 400, so as to reduce the cross-sectional surface area of the retractor 100. When pushed into the operative trochar 400, the membrane 104 of the retractor 100 is compressed and/or sandwiched between the two opposing portions of the frame 102 of the retractor 100. Alternatively, the membrane 104 of the retractor 100 may be wrapped around the frame 102 of the retractor 100 when the retractor 100 is in a collapsed configuration. After completing the procedure, the PH device 300 is reinserted into the abdomen via the trochar 400 and the retrieving portion 308 of the coupling portion 305, such as the "u" shaped retrival hook 309, at the distal end region 304 of the PH device 300 couples to a portion of the frame 102 of the retractor 100 to pull the retractor 100 out of the abdomen through the trochar 400.

Figure 14:
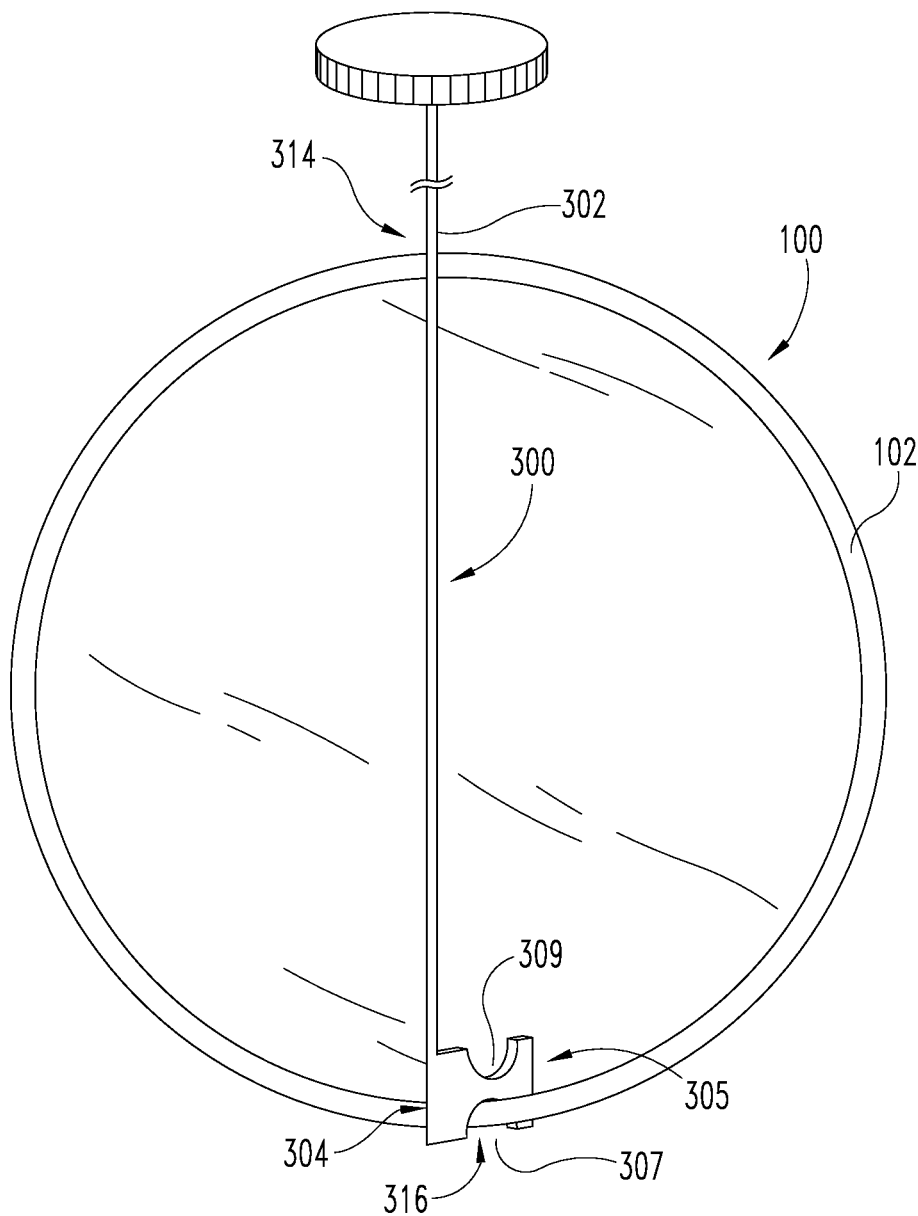
FIG. 14 is a front elevational view of a delivery device releasably coupled to a deformable resilient retractor in an expanded configuration.
Figure 15:
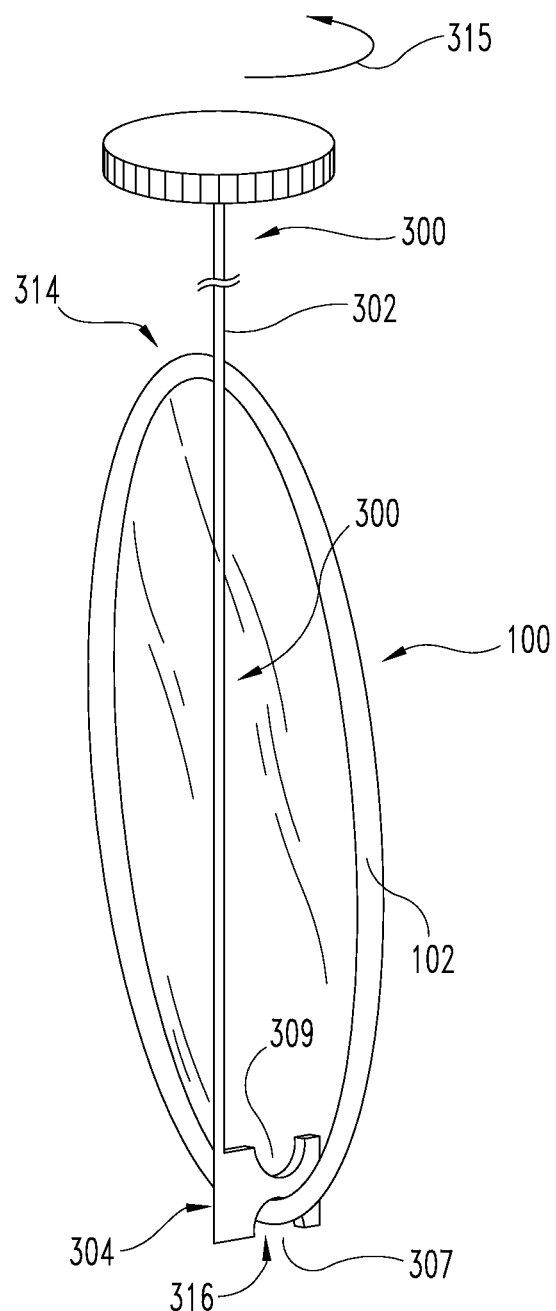
FIG. 15 is a front elevational view of a delivery device releasably coupled to a deformable resilient retractor in an elongated configuration.

In another embodiment, to enable the retractor 100 to be inserted through a standard 12 mm operative trochar 400, the frame 102 of a retractor 100 has a maximum diameter of 5 mm. Additionally, in some instances, it may be preferable that the frame 102 have a hemispherical cross-section. The retractor 100 can be twisted around a PH device 300 to form a helical arrangement, sometimes referred to as a "twizzler" shape, to minimize the maximum outer dimension of the retractor 100. Referring to FIG. 14, similar to the PH device 300 of FIG. 12, the distal end region 304 of the PH device 300 has a coupling portion 305 that may comprise hooks 307 and 309 located at and/or near the distal tip of the PH device 300. In some embodiments, the coupling portion 305 is arranged for twistable coupling of the retractor 100 to the PH device 300 such that one or more portions of the retractor 100 may be twisted and/or rotated with respect to the PH device 300 when a portion of the retractor 100 is coupled to the PH device 300. In some instances, at the tip of the pusher is an inverted ("n" shaped) hook 307 arranged to stabilize a distal aspect of the retractor 100 during twisting of the frame 102 and/or to push a portion of the retractor 100 through a trochar 400 during insertion into the body of a patient (e.g., beneath the skin of a patient).

Figure 16:
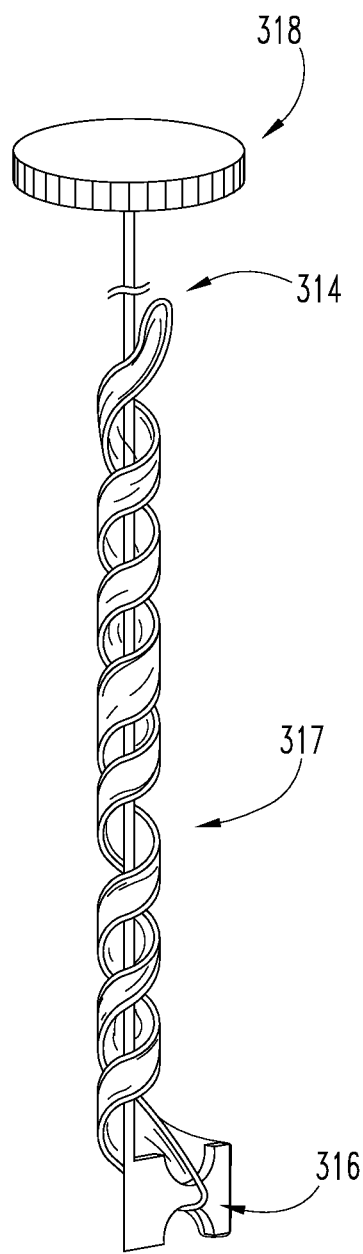
FIG. 16 is a front elevational view of a deformable resilient retractor helically coiled around a delivery device.

To create the twisted arrangement of the retractor 100 around one or more portions of the PH device 300, resembling a "twizzler" as shown in FIG. 16, the frame 102 of the retractor 100 is extended and/or stretched proximally substantially along the axis of the shaft 302 of the PH device 300 so as to configure the retractor 100, including frame 102, into an elongated profile. The proximal end 314 of the frame 102 is rotated in a clockwise or anti-clockwise direction 315, while the distal end 316 is prevented from rotating by means of the coupling portion 305 such as hook 307 located near and/or at the tip of the shaft 302 of the PH device 300. The twisting is continued until the retractor 100 has been satisfactorily elongated in its axial plane and contracted and/or compressed in its maximum outer dimension in the transverse plane, such as by a decreased cross-sectional surface area. The resulting configuration resembles a helically wound, sometimes referred to as a "twizzler", configuration 317, as shown in FIG. 16. In some instances, the frame 102 of the retractor 100 forms a double helix that extends along a length of the PH device 300. The twisting can be accomplished by any means apparent to one of ordinary skill in the art, such as by a rotatable screw and/or a threaded device 318 located on the proximal aspect of the shaft 302. In some instances, the screw and/or knob 318 may be made unidirectional by means of ratchets to prevent unfurling of a portion of the retractor 100 such as the frame 102.

In an alternative embodiment to create the helically wound and/or coiled configuration, aka the "twizzler", the frame 102 of the retractor 100 is stretched and/or extended proximally substantially along the axis of the shaft 302, to make an elongated profile. The distal end 316 of the frame 102 is then rotated in a clockwise or anti-clockwise direction 315 around the shaft 302 of the PH device 300, whilst the proximal end 314 is prevented from rotating around a portion of the PH device 300. In yet another embodiment, to create the "twizzler", the frame 102 is stretched and/or extended proximally substantially along the axis of the shaft 302, to make an elongated profile. The proximal end 314 of the frame 102 is then rotated in a clockwise or anti-clockwise direction 315, whilst the distal end 316 is rotated in the opposite direction.

After creating the helically coiled arrangement of the retractor 100, the distal end 316 is simply advanced (e.g., pushed) through the operative access device, such as a trochar 400, whereupon it opens up in the peritoneal cavity once it exits the distal end of the access device, e.g., trochar 400. The triangular or hemispherical cross section profile of the frame 102 forms a generally circular profile when the frame 102 is twisted into its helically-coiled shape, so as to reduce the cross-sectional surface area. When pushed into the operative access device, the membrane 104 of the retractor 100 is compressed and/or sandwiched between the two opposing sides of the frame 102 of the retractor 100. Alternatively, the membrane 104 of the retractor 100 may be wrapped around the frame 102 of the retractor 100 in its stretched and/or extended configuration when advanced (e.g., pushed) into the operative access device (e.g., trochar 400). After completing the procedure the PH device 300 is readvanced and/or reinserted into the operative access device and the retrieving portion 308 of the coupling portion 305, such as the "u" shaped retrieval hook 309 at and/or near the tip of the pusher, couples and/or hooks a portion of the retractor 100, such as the frame 102, to retrieve (e.g., pull) it out of the abdominal cavity.

To simplify the helical coiling (e.g., twisting) of the retractor, in some embodiments, the retractor is pre-assembled and inserted into an outer sheath or cylinder in a helically wound (e.g., "twizzler") configuration. In some instances, the outer sheath or cylinder is slightly less than 12 mm in diameter. No shaft 302 of the PH device 300 may be necessary in the final assembled product in this arrangement. The sheath-retractor assembly can be inserted into the operative trochar 400 and the retractor is simply advanced (e.g., pushed) out of the sheath by a simple pushing device. The retractor 100 may be retrieved in the same way as the embodiments described above.

The PH device 300 can be made of biocompatible metal, polymer or a combination thereof. The shaft 302, hooks 307 and/or 309, and knob can adopt any reasonable size with desirable physical integrity. For example, the shaft 302 can have a diameter of about 1 mm to 3 mm. Additionally, in some instances, the portions of the retractor 100 are arranged to receive portions of the PH device 300. For instance, there may be an aperture in the membrane 104 of the retractor 100 to receive a portion of the PH device 300 so that the PH device 300 does not puncture and/or damage the membrane 104 during coupling of the coupling portion 305 with a portion of the retractor 100.

The PH device 300 in general can be used to facilitate the delivery and/or retrieval of the retractors described herein. As depicted in FIG. 12, the PH device 300 in general can have a coupling portion 305 comprising an inserting portion 306 and/or a retrieving portion 308 arranged to insert and/or retrieve a portion of a retractor 100 into and/or out of the body of a patient (e.g., beneath the skin of a patient). In some instances, the coupling portion 305 comprises a pusher hook 307 and/or a retrieval hook 309. The portions of the coupling portion 305, such as the inserting and/or retrieving portions 306 and/or 308 comprising hooks 307 and 309, however, can be positioned at different locations on the shaft 302, not necessarily adjacent each other as shown in FIG. 12. Additionally, the size, shape, and the number of the portions of the coupling portion 305, such as hook(s) 307 and/or 309 positioned at the distal end of the shaft of the PH device 300, may vary to suit different surgical needs. In some embodiments, the PH device 300 may have only one portion, such as inserting portion 306 and/or pusher hook 307, to facilitate the delivery of one or more retractors 100. In other embodiments, the PH device 300 may have only a retrieving portion 308 in the coupling portion 305, such as one retrieval hook 309, to facilitate the retrieval of one or more retractors 100. The portions of the PH devices 300 such as the inserting portion 306, retrieving portion 308, "n" shaped pusher hook 307, and/or "u" shaped retrieval hook 309 can be used singly or in combination to facilitate the delivery and/or the retrieval processes of one or more retractors 100. In some embodiments, one or more of the portions of the coupling portion 305 may be removable. For example, the pusher hook 307 can be removed after being used to facilitate the delivery of one or more retractors 100, leaving only the retrieval hook 309 to be used in the retractor 100 retrieval process.

Alternatively, the PH device 300 may start with fewer than all of the portions of the coupling portion 305, such as only the inserting portion 306 comprising pusher hook 307, to be used to facilitate the delivery of the retractors 100, and, upon completion of the delivery process, the inserting portion 306 is removed and a the retrieving portion 308 (e.g., retrieval hook 309) is adapted onto the shaft 302 of the PH device 300 so the PH device 300 is now suitable to facilitate the subsequent retrieval process. The shaft 302 of the PH device 300 in general is straight. Although curvature can be built into the shaft 302 to adapt the PH device 300 for appropriate surgical applications. The PH device 300 described herein can be used to facilitate the delivery and retrieval of retractors 100 through a variety of surgical openings and is not limited to be used in conjunction with trochar 400 only.

Disclosed Retractor in Surgical Applications

Figure 6A:
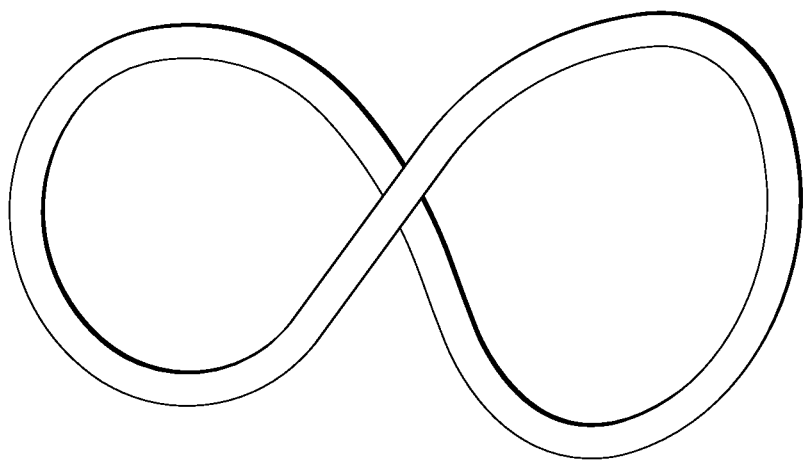
FIG. 6a is an illustration of the retractor of FIG. 1 twisted into a figure of 8 configuration.

A circular retractor can be used in abdominal surgeries by twisting the retractor into a folded shape, such as a figure-eight shape or other convenient folded shape. For example, a figure eight shape formed from a circular retractor can be further folded upon itself to make it approximately half its original diameter. Non-circular shaped retractors can be similarly appropriately folded for insertion into the patient. The folded or deformed retractor can then be inserted into a small laparoscopic incision into the peritoneal cavity. Having inserted the retractor into the peritoneal cavity, the retractor "unfurls" and assumes substantially its original size and retracts small bowel out of the pelvic cavity. As shown in FIG. 6a, a circular retractor 100 of FIG. 1 is folded into a figure-of eight shape, which when folded upon itself forms a two layered circular structure with about half of its original diameter, as shown in FIG. 6b. When released, the deformed retractor can substantially regain its resting configuration, and the particular resulting shape and size of the deformable retractor can conform to the peritoneal cavity into which it is placed.

The resilient retractor when deformed can be inserted into smaller incisions than would otherwise be possible. The unfolding of the deformed retractor to assume substantially its original size inside a body cavity allows the retractor to push against the wall of the cavity to become self-retainable inside the cavity. The resiliency is generally not excessive so that the retractor does not injure any organs or the wall of the body cavity.

Specifically, for use in the abdominal cavity, the retractor can be compressed in the anterior-posterior (A-P) plane by pressure from the anterior abdominal wall into an ovoid shape, and further bent in the lateral plane into a convex or non-planar "U" form, by pressure from the lateral abdominal wall. In some embodiments, the retractor is positioned for and capable to support organs in a vertical plan (e.g., preventing movement of organs along a superior to inferior direction and/or vice versa in the abdominal cavity). Although convex deployed configuration is discussed, it is understood that other deployed configurations such as planar or concave relative to the lower part of the patient are also contemplated and within the present disclosure. The resulting two dimensional pressures not only distribute the pressures substantially along the entire circumference of the retractor to reduce or prevent organ injury or excessive local pressure at any one location, but also maintain the retractor in place without additional external force or devices. In addition, as the retractor tries to assume its original configuration and conforms to the inner contours of the abdominal cavity, the membrane expands in an anterior-posterior and lateral direction to serve as the retractor surface in the axial plane, which effectively occludes the abdominal cavity, retracts viscera out of the pelvis, and thereby prevents the small bowel from entering the surgical field. The retractor provides retraction in all three planes and is self retaining. In some embodiments, it may be desirable to use a retractor that has a natural non-planar convex shape in the undeformed or resting configuration. When such a non-planar convex shaped retractor is released inside a body cavity, it regains substantially its convexity and pushes organs away to create desired working space.

By avoiding significant pressure being applied to the retroperitoneum and by the distribution of pressure around the entire periphery of the retractor, the great vessels in the retroperitoneum (vena cava and aorta) are not significantly impinged, compressed or obstructed. This use of the device avoids arterial insufficiency (which results from aortic compression) and also avoids impeding venous return (which results from vena caval compression), both of which can be potentially life threatening. In some embodiments, the deployed circular retractor or other suitable device design avoids trauma to or compression of the retroperitoneal structures during sudden deflation of the abdomen, which can happen from time to time during laparoscopic surgery. In this event, the retractor simply distorts to a more ovoid shape exerting little or no additional force on the retroperitoneum or viscera. Additionally, the retractor avoids pressure necrosis or even perforation of small bowel or other delicate viscera. The reduction or elimination of compression or occlusion of the major blood vessels avoids a potential drop in blood pressure, which can be a life-threatening problem with metal mechanical retractors known in the art. In a further embodiment, the retractor may be bean shaped to provide the concavity of the bean over the retroperitoneum to further reduce compression of the great vessels.

Figure 8B:
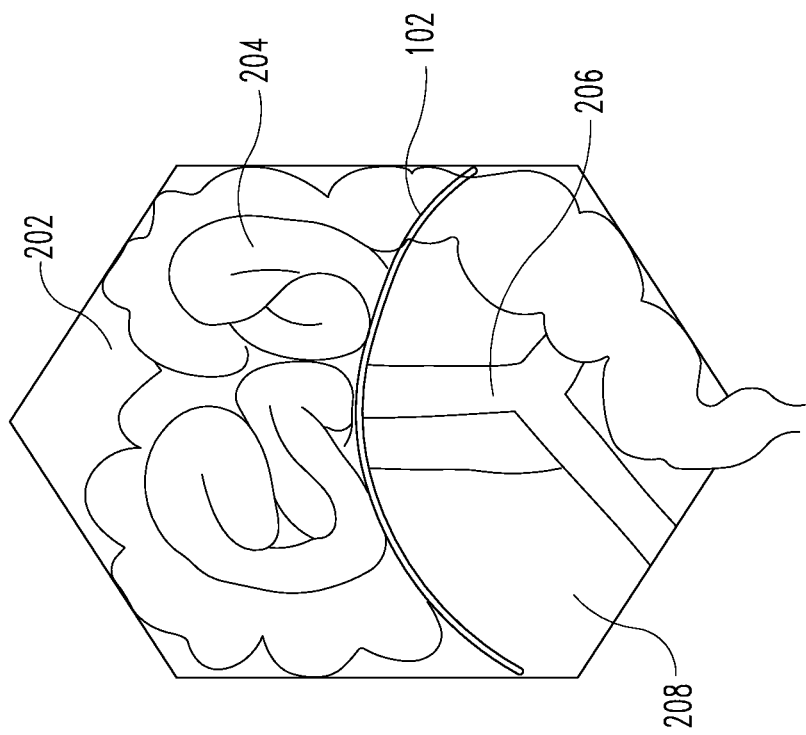
FIG. 8b is a schematic diagram of peritoneal cavity of FIG. 8a with a retractor deployed in a convex shape inside the cavity making a working space.
Figure 8A:
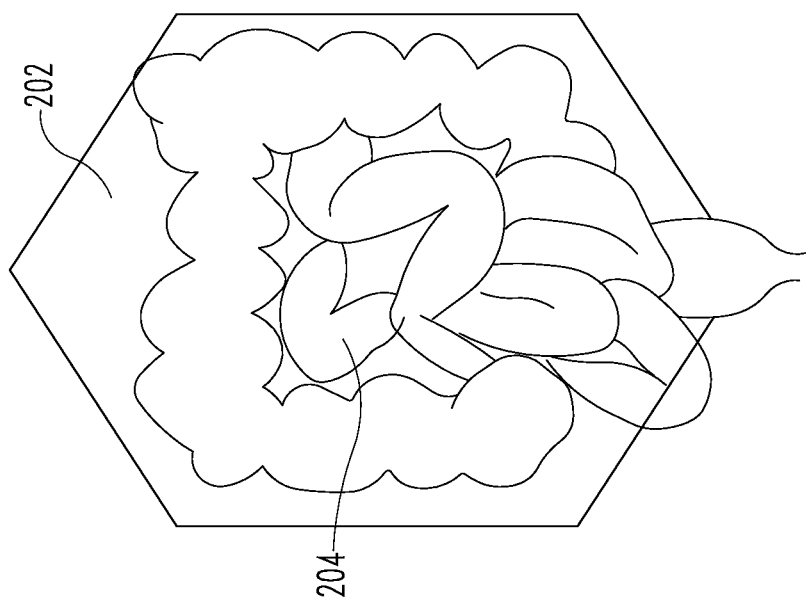
FIG. 8a is a schematic diagram of peritoneal cavity showing viscera.

Referring to FIG. 8a, a schematic diagram of abdominal cavity 202 is shown with bowel loops 204 inside the pelvic cavity. A circular retractor placed inside the abdominal cavity is shown in FIG. 8b, whereupon it gently "unfurls" to assume substantially its original size. As a result of the resilient frame 102, the retractor assumes the contours of the inner aspect of the patients inner abdominal wall and forms a convex shape to effectively retract bowel loops into the upper abdominal cavity and prevent them from falling into pelvic cavity where surgery can be performed. As a result of the contraction, a working space 208 is created inside the pelvic cavity exposing great vessels 206. After completion of the surgery, the retractor is gently pulled out of the incision, and its flexible nature avoids any injury to the abdominal viscera or the incision itself. Once inside the abdominal cavity, the retractor is released and effectively retain organ. The working space created by the retractor is substantially free from the retained organs, thus providing improved access to surgical site of interest.

In some embodiments, the 3-D retractor can be rotated around the peritoneal cavity or around the inner ring of the abdominal wound retractor to provide access to the left colon or splenic flexure for the purpose of surgical mobilization, whilst still retracting the viscera out of the surgical field. For this purpose, the retractor is rotated counter-clockwise within the peritoneal cavity. The retractor may also be rotated or repositioned to enable mobilization of the right colon and hepatic flexure, again keeping the viscera out of the surgical field. For this purpose, the retractor is rotated clockwise within the peritoneal cavity.

Figure 7:
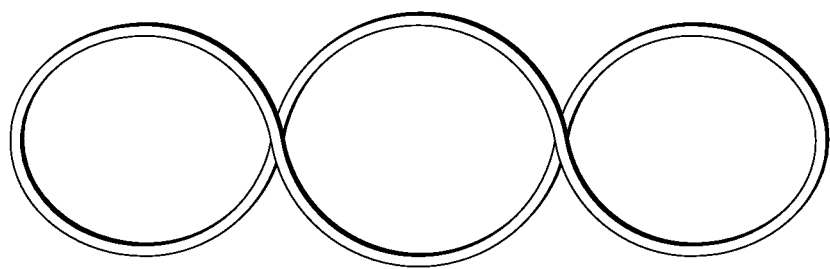
FIG. 7 is a schematic diagram of the retractor of FIG. 1 folded into a three consecutive oval shape.

In some embodiments, the lateral one thirds of a circular resting retractor may be individually "twisted" 180 degrees in their axial plane, preferably one in a clockwise and the other in a counter-clockwise manner This forms a symmetrical shape of three serial ovoids: A central ovoid, and two lateral ovoids as shown in FIG. 7. When each lateral ovoids are released, they untwist in the opposite directions, when viewed end-on from one direction. Since both lateral ovoids are located at diametrically opposing ends of the central ovoid, the lateral ovoids "untwist" in a mirror image manner of each other. The end result of this is that the retractor untwists in a symmetrical manner when viewed side-on, to providing a symmetrical and effective retractor capable of retracting bowel out of the pelvis. Having formed both lateral ovoids, each lateral ovoid may then be folded 180 degrees to overlay the central ovoid, resulting in a 3-layer, generally circular or ovoid shape, one third of the original diameter. When the 3-layer deformed retractor is inserted into peritoneal cavity, the two lateral one third "ovoids" unfurl laterally and untwist axially to assume the generally U shaped retractor configuration detailed above. Of course, for a particular use and for particular device configuration if not circular, the particular folding of the surgical retractor can be selected appropriately by the practitioner based on the teachings herein. The deployed retractor may also adopt a concave shape directing the bowel or other organs toward the head, or a planar shape inside the body cavity, which can be particularly effective for embodiments of membranes that are essentially not elastic.

The aforementioned twisting and folding maneuver can be repeated a plurality of times, to further decrease the diameter of the retractor for example to one quarter, one eighth, or one sixteenth etc of the original resting configuration. This smaller configuration of the retractor facilitates insertion of the retractor into the peritoneal cavity via an abdominal wound retractor or hand assisted laparoscopic access retractor. For example, the retractor can be used in conjunction with a SILS access device by Covidien or a plastic HALS retractor such as the "Dextrus" by Ethicon Endosurgery, or with the "Lexus" HALS retractor made by Applied Medical. This combination provides much improved surgical exposure and is highly desirable during laparoscopic surgeries.

Figure 17B:
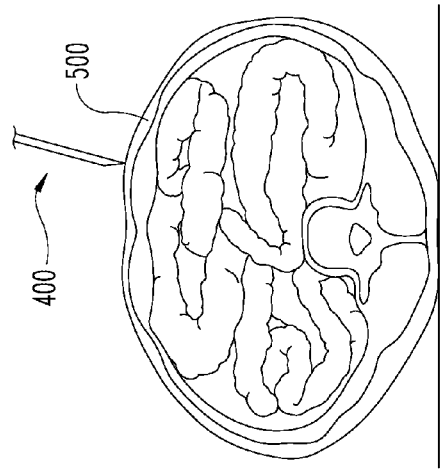
FIG. 17b illustrates an access device being advanced towards the skin of the patient.
Figure 17D:
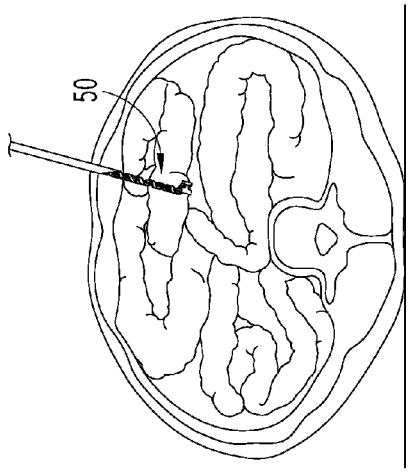
FIG. 17d illustrates a deformable resilient retractor being advanced by a delivery device through the access device.
Figure 17A:
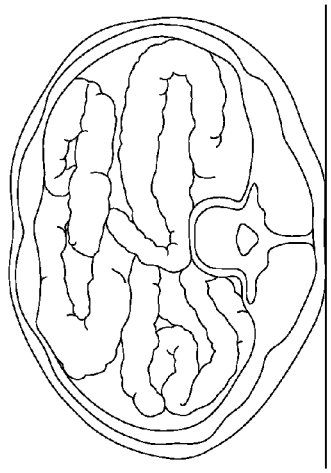
FIG. 17a is a cross-sectional view of the abdomen of the patient taken along the coronal plane.
Figure 17C:
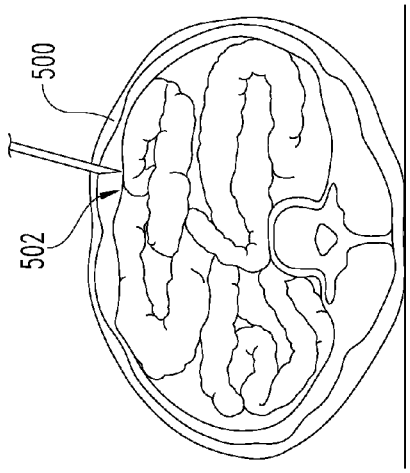
FIG. 17c illustrates an access device penetrating the skin and abdominal wall of a patient and accessing the abdominal cavity.
Figure 17E:
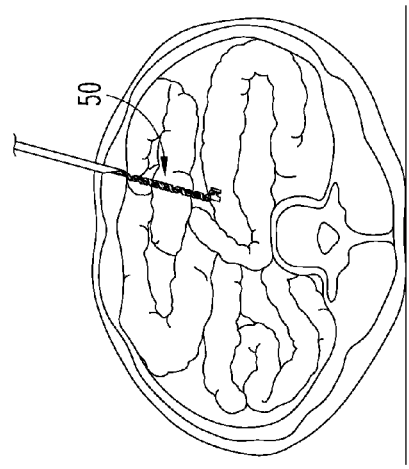
FIG. 17e illustrates the deformable resilient retractor in a contracted configuration prior to configuring into an expanded configuration.
Figure 17F:
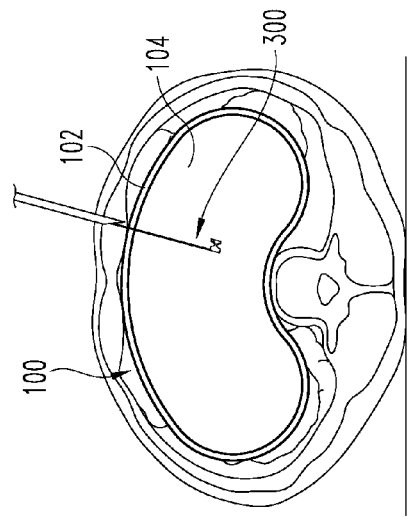
FIG. 17f illustrates the deformable resilient retractor in an expanded configuration.
Figure 17G:
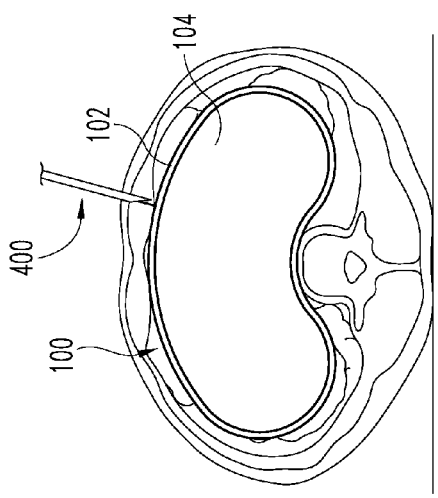
FIG. 17g illustrates the deformable resilient retractor and access device after withdrawal of the delivery device.

One exemplary method of deploying a retractor, such as a deformable resilient retractor, will now be briefly described with reference to FIGS. 17a-g. FIGS. 17a-g illustrate the abdominal cavity of a patient as viewed along a inferior to superior direction. As illustrated in FIG. 17b, an access device such as a trochar 400 is advanced towards the outer surface of the skin 500 of a patient. As the tip of the trochar 400 penetrates the skin 500 and the abdominal wall, the trochar 400 gains access to the abdominal cavity 502. A retractor system 50 comprising a retractor and/or an accessory such as a push-and-hook type delivery device can then be advanced through a lumen of the trochar 400. In some instances, the retractor system 50 is advanced substantially along an anterior to posterior direction. Once the retractor system 50 is in the desired position within the body of the patient, the retractor 100 is released and one or more portions of the retractor 100, such as the frame 102, self-extend so as to spread the membrane 104 into a spread-open configuration. After the retractor 100 is in an expanded configuration and the operator is satisfied with the retraction of organs from the target surgical area, any delivery device associated with the retractor system 50, such as the PH device 300 may be withdrawn from the abdominal cavity through the lumen defined by the trochar 400, to a position outside of the body. A lumen of the trochar can also be used to perform additional surgical procedures.

While the invention has been illustrated and described in detail in the drawings and foregoing description, the same is to be considered as illustrative and not restrictive in character, it being understood that the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

What is claimed is:

1. A biocompatible retractor, comprising:
   a retractor body comprising a deformable resilient frame that extends around and defines a central opening surrounded by the frame and a deformable membrane coupled to said deformable resilient frame and extending across a portion of said central opening;
   wherein said central opening has a circumferential length;
   wherein said deformable resilient frame is arranged to vary the circumferential length of the central opening, said deformable resilient frame having a first end slidably received within an opening defined by a second end of the deformable resilient frame and said deformable resilient frame being self-expandable from a contracted configuration to an expanded configuration; and
   wherein the retractor body is arranged for complete disposal within the body of a patient.

2. The biocompatible retractor of claim 1, further comprising:
   a biasing member coupling a first portion and a second portion of said deformable resilient frame.

3. The biocompatible retractor of claim 2, wherein:
   said biasing member comprises a spring.

4. The biocompatible retractor of claim 2, wherein:
   said biasing member is positioned within said resilient frame.

5. The biocompatible retractor of claim 1, further comprising:
   an insert coupled to said deformable resilient frame.

6. The biocompatible retractor of claim 5, wherein:
   said insert is positioned within said resilient frame.

7. The biocompatible retractor of claim 1, wherein said deformable resilient frame extends around said central opening.

8. A biocompatible retractor for insertion beneath the skin of a patient, comprising:
   a retractor body comprising a deformable resilient frame that extends around and defines a central opening surrounded by the frame and a deformable membrane coupled to said deformable resilient frame and extending across a portion of said central opening;
   wherein said deformable resilient frame has a first end slidably received within an opening defined by a second end of the deformable resilient frame and said deformable resilient frame is telescopically configurable between a contracted configuration and an expanded configuration arranged to retract tissue;
   wherein said deformable resilient frame is self-expandable from a contracted configuration to an expanded configuration;
   wherein said contracted configuration is arranged for laparoscopic insertion through the skin of a patient; and wherein said deformable resilient frame in said expanded configuration and said deformable membrane are arranged for complete disposal within the body of a patient.

9. The biocompatible retractor of claim 8, wherein:
said deformable resilient frame in said contracted configuration comprises an elongated arrangement.

10. The biocompatible retractor of claim 8, wherein:
said deformable resilient frame in said contracted configuration is helically coiled.

11. The biocompatible retractor of claim 10, wherein:
said deformable resilient frame in said contracted configuration forms a double helix.

12. An assembly for delivering a retractor beneath the skin of a patient, comprising:
an elongated body comprising a proximal end region, a distal end region, and a retractor coupling portion positioned in said distal end region; and
a deformably resilient retractor comprising a deformable resilient frame and a deformable membrane coupled to the deformable resilient frame, said deformably resilient retractor helically wound around said elongated body;
wherein said retractor coupling portion is coupled to a portion of said deformably resilient retractor; and
wherein said retractor coupling portion is arranged to move said portion of said deformably resilient retractor between a first position outside of the body of the patient and a second position beneath the skin of the patient.

13. The assembly of claim 12, further comprising:
a first recess defined by said retractor coupling portion and arranged to receive the portion of the deformably resilient retractor.

14. The assembly of claim 13, wherein:
said first recess opens away from the proximal end region of said elongated body and is arranged to push the portion of the deformably resilient retractor into the second position.

15. The assembly of claim 13, further comprising:
a second recess defined by said retractor coupling portion and opening away from said distal end region of said elongated body and arranged to pull a portion of the deformably resilient retractor from the second position towards the first position.

16. The assembly of claim 12, wherein:
said retractor coupling portion is arranged for twistably coupling a portion of the deformably resilient retractor.

* * * * *